United States Patent
Belbruno et al.

(10) Patent No.: US 11,366,077 B2
(45) Date of Patent: Jun. 21, 2022

(54) SYSTEMS, SENSING DEVICES AND METHODS FOR DETECTION OF AIRBORNE CONTAMINANTS

(71) Applicant: The Trustees of Dartmouth College, Hanover, NH (US)

(72) Inventors: Joseph J. Belbruno, Hanover, NH (US); Susanne E. Tanski, Grantham, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 344 days.

(21) Appl. No.: 14/407,860

(22) PCT Filed: Jun. 13, 2013

(86) PCT No.: PCT/US2013/045673
§ 371 (c)(1),
(2) Date: Dec. 12, 2014

(87) PCT Pub. No.: WO2013/188675
PCT Pub. Date: Dec. 19, 2013

(65) Prior Publication Data
US 2015/0132857 A1    May 14, 2015

Related U.S. Application Data

(63) Continuation-in-part of application No. 13/495,258, filed on Jun. 13, 2012, which is a continuation-in-part
(Continued)

(51) Int. Cl.
*G01N 27/12* (2006.01)
*G01N 33/00* (2006.01)

(52) U.S. Cl.
CPC ....... *G01N 27/126* (2013.01); *G01N 33/0073* (2013.01); *Y10T 436/145555* (2015.01);
(Continued)

(58) Field of Classification Search
CPC ... G01N 31/22; G01N 27/126; G01N 33/0073
See application file for complete search history.

(56) References Cited

U.S. PATENT DOCUMENTS

| 5,208,301 | A | * | 5/1993 | Epstein | C08G 73/0266 525/534 |
| 5,244,562 | A | * | 9/1993 | Russell | A61B 5/14532 204/403.06 |

(Continued)

FOREIGN PATENT DOCUMENTS

| CN | 101776635 | 7/2010 |
| KR | 100977292 B1 | 8/2010 |

(Continued)

OTHER PUBLICATIONS

Sambe, et al., "Uniformly-Sized, Molecularly Imprinted Polymers For Nicotine by Precipitation Polymerization," Journal of Chromatography A 1134, pp. 88-94, Sep. 2006.
(Continued)

*Primary Examiner* — Brian R Gordon
*Assistant Examiner* — Dwan A Gerido
(74) *Attorney, Agent, or Firm* — Lathrop GPM LLP

(57) ABSTRACT

A device for detecting airborne contaminants includes a protonated, electrically conductive sensing material with affinity for binding with, and capable of being deprotonated by, the airborne contaminant. Electronics measure a property of the sensing material that is sensitive to deprotonation and generates signals indicative of the airborne contaminant. A method for detecting airborne contaminants includes: determining a property change of the protonated, electrically conductive material; and determining presence of the airborne contaminant based on the change. A system for detecting airborne contaminants includes: a data center in remote communication with multiple sensing devices each having: protonated, electrically conductive sensing material
(Continued)

with affinity for binding with, and capable of being deprotonated by, an airborne contaminant, and electronics for relaying signals indicative of a sensing material deprotonation property to the data center; and wherein a user associated with a sensing device is notified of an abnormal level of the airborne contaminant.

6 Claims, 19 Drawing Sheets

Related U.S. Application Data of application No. PCT/US2011/051169, filed on Sep. 12, 2011.

(60) Provisional application No. 61/466,101, filed on Mar. 2, 2011, provisional application No. 61/381,512, filed on Sep. 10, 2010.

(52) U.S. Cl.
CPC ............... *Y10T 436/200833* (2015.01); *Y10T 436/202499* (2015.01); *Y10T 436/205831* (2015.01)

(56) References Cited

U.S. PATENT DOCUMENTS

| | | | | |
|---|---|---|---|---|
| 5,252,292 | A * | 10/1993 | Hirata | G01N 27/126 204/400 |
| 5,536,473 | A | 7/1996 | Monkman et al. | |
| 5,587,273 | A * | 12/1996 | Yan | G01N 33/54373 430/269 |
| 5,607,573 | A * | 3/1997 | Miller | G01M 3/16 204/415 |
| 6,046,054 | A | 4/2000 | McGeehin et al. | |
| 6,582,971 | B1 | 6/2003 | Singh et al. | |
| 6,807,842 | B2 | 10/2004 | Williams et al. | |
| 7,469,076 | B2 | 12/2008 | Carlson | |
| 8,615,374 | B1 * | 12/2013 | Discenzo | G06F 15/00 219/497 |
| 2003/0004426 | A1 * | 1/2003 | Melker | G01N 29/022 600/532 |
| 2004/0072359 | A1 | 4/2004 | Southard | |
| 2004/0126814 | A1 | 7/2004 | Singh et al. | |
| 2005/0019218 | A1 * | 1/2005 | Murray | G01N 21/6428 422/82.08 |
| 2005/0064154 | A1 | 3/2005 | Aylward et al. | |
| 2005/0126909 | A1 * | 6/2005 | Weiller | G01N 27/126 204/418 |
| 2005/0150778 | A1 * | 7/2005 | Lewis | G01N 27/126 205/777.5 |
| 2006/0079648 | A1 | 4/2006 | Lutsen et al. | |
| 2007/0087564 | A1 | 4/2007 | Speakman | |
| 2008/0041138 | A1 | 2/2008 | Marra | |
| 2008/0093226 | A1 | 4/2008 | Briman et al. | |
| 2008/0150556 | A1 | 6/2008 | Han et al. | |
| 2009/0054799 | A1 * | 2/2009 | Vrtis | G01N 33/497 600/532 |
| 2009/0115605 | A1 | 5/2009 | Ravenis et al. | |
| 2010/0000883 | A1 | 1/2010 | Morrin et al. | |
| 2010/0039124 | A1 | 2/2010 | Belbruno et al. | |
| 2010/0193376 | A1 | 8/2010 | Ruis et al. | |
| 2010/0214252 | A1 | 8/2010 | Wu | |
| 2011/0045601 | A1 | 2/2011 | Gryska et al. | |
| 2011/0111350 | A1 | 5/2011 | Lakshmi et al. | |
| 2011/0159519 | A1 | 6/2011 | Schmidt et al. | |
| 2011/0241260 | A1 | 10/2011 | Hong et al. | |
| 2012/0006102 | A1 | 1/2012 | Bryant et al. | |
| 2012/0214252 | A1 | 8/2012 | Knop | |
| 2012/0270330 | A1 * | 10/2012 | Tao | G01N 29/022 436/140 |
| 2012/0285833 | A1 | 11/2012 | Liu et al. | |
| 2014/0227795 | A1 | 8/2014 | Belbruno | |

FOREIGN PATENT DOCUMENTS

| | | |
|---|---|---|
| WO | 2008007359 A2 | 1/2008 |
| WO | 2008045596 A2 | 4/2008 |
| WO | 2008063204 A2 | 5/2008 |
| WO | 2011136548 A3 | 11/2011 |
| WO | 2012034115 | 3/2012 |

OTHER PUBLICATIONS

PCT Application PCT/US2013/045673 International Search Report and Written Opinion, dated Sep. 2, 2013, 16 pages.
Sotzing, Gregory A., et al., "Highly Sensitive Detection and Discrimination of Biogenic Amines Utilizing Arrays of Polyaniline/Carbon Black Composite Vapor Detectors," Chem. Mater. vol. 12, No. 3, pp. 593-595, 2000.
Belbruno, et al., Sensor and Actuators, vol. 155(2), pp. 915-918, Feb. 2, 2011.
PCT Patent Application PCT/US2012/053119 International Search Report and Written Opinion, dated Feb. 27, 2013, 3 pages.
Thoelen, et al., "A MIP-Based Impedimetric Sensor For the Detection of Low-MW Molecules," Biosensors and Bioelectronics, vol. 23, pp. 913-918, 2008.
PCT Patent Application PCT/US2011/051169 International Search Report dated Jan. 3, 2012, 6 pages.
U.S. Appl. No. 13/495,258 select file history dated Jun. 21, 2013 to Apr. 21, 2015, 142 pages.
Liu, Yang, et al., The Development of Chloride Ion Selective Polypyrrole Thin Film On A Layer-by-Layer Carbon Nanotube Working Electrode, Proc. of SPIE., vol. 7983, pp. 798315-1 to 798315-9, 2011.
U.S. Appl. No. 14/342,059 Office Action dated Feb. 25, 2015, 18 pages.
U.S. Appl. No. 13/495,258, Notice of Allowance dated Apr. 22, 2016, 9 pages.
PCT Application PCT/US2012/053349 International Search Report and Written Opinion, dated Feb. 7, 2013, 16 pages.
U.S. Appl. No. 13/495,258 Office Action/Final Rejection dated Aug. 13, 2015, 11 pages.
U.S. Appl. No. 13/495,258 Office Action dated Dec. 22, 2015, 13 pages.
Office Action dated Oct. 7, 2016, corresponding to U.S. Appl. No. 14/554,634, 11 pages.
Final Rejection in U.S. Appl. No. 14/954,142 dated Jan. 11, 2018, 10 pp.
U.S. Appl. No. 14/554,634, Office Action dated Nov. 20, 2017 (13 pages).
U.S. Appl. No. 14/954,142, Office Action dated Aug. 29, 2017 (23 pages).
U.S. Appl. No. 14/554,634; Office Action dated Mar. 7, 2019—15 pgs.
Non-Final Rejection in U.S. Appl. No. 16/004,297 dated Nov. 20, 2019, 14 pp.

* cited by examiner

SYSTEMS, SENSING DEVICES AND METHODS FOR DETECTION OF AIRBORNE CONTAMINANTS

CROSS-REFERENCE TO RELATED APPLICATIONS

The present application is a continuation in part of U.S. patent application Ser. No. 13/495,258 filed Jun. 13, 2012, which is a continuation in part of PCT Patent Application No. PCT/US2011/051169 filed Sep. 12, 2011, which claims the benefit of priority from U.S. Provisional Application No. 61/466,101 filed Mar. 2, 2011 and from U.S. Provisional Application No. 61/381,512 filed Sep. 10, 2010. All of the above-identified applications are incorporated herein by reference in their entireties.

BACKGROUND

Certain airborne contaminants pose serious human health risks. Hazardous airborne contaminants are found in tobacco smoke and in outgassing from common materials in the local environment, and are generated by natural processes such as combustion. Hazardous airborne contaminants are found in a number of settings regularly encountered by average people. A prominent example of hazardous airborne contaminants is nicotine and outgassing byproducts of cigarette smoke, such as formaldehyde. There is in fact no safe level of secondhand smoke exposure as it increases risk of cancer, cardiovascular disease, and childhood illnesses. These same contaminants constitute health risks even in the form of third-hand smoke, due to outgassing from materials exposed to cigarette smoke. Formaldehyde outgasses from widely used building materials including pressed wood and paint and household products such as cleaners and paper towels, and is a combustion by-product. Formaldehyde has been classified as a likely carcinogen by the U.S. Environmental Protection Agency, and workplace exposure is strictly regulated. It is further suspected to cause damage to reproductive systems and chronic exposure may lead to reduced immune response.

In the case of nicotine and other components in cigarette smoke, the prior art does not provide real-time monitoring solutions. While conventional technologies measure nicotine and particulate matter in indoor environments, such technologies involve large air sampling devices that actually impair immediate feedback, because complex laboratory procedures are required to quantify samples. Moreover, complex sampling techniques and instrumentation are required to obtain and measure adsorbed material affected by smoke.

SUMMARY

In accord with the teachings herein, systems, sensing devices and methods for detecting airborne contaminants monitor the presence and/or concentration of such contaminants, and in real-time. Devices constructed according to the teachings herein may aid individual health by encouraging avoidance of the contaminants as well as closure of the processes generating them.

In one embodiment, a device detects an airborne contaminant. The device includes a protonated, electrically conductive sensing material with an affinity for binding with, and capable of being deprotonated by, the airborne contaminant. Electronics of the device measure a property of the sensing material that is sensitive to deprotonation and generate signals indicative of the airborne contaminant.

In one embodiment, a method for detecting at least one airborne contaminant includes determining change in a property of protonated, electrically conductive material exposed to ambient air with the airborne contaminant; and determining presence of the airborne contaminant based on the change.

In one embodiment, a system for detecting airborne contaminants includes a data center and a plurality of sensing devices in remote communication with the data center. Each of the sensing devices has: (a) protonated, electrically conductive sensing material with an affinity for binding with, and capable of being depronated by, at least one of the airborne contaminants, and (b) electronics for relaying signals indicative of a sensing material deprotonation property to the data center; and wherein a user associated with any one of the sensing devices is notified of abnormal level of at least one of the airborne contaminants.

DETAILED DESCRIPTION OF DRAWINGS

Figure 1:
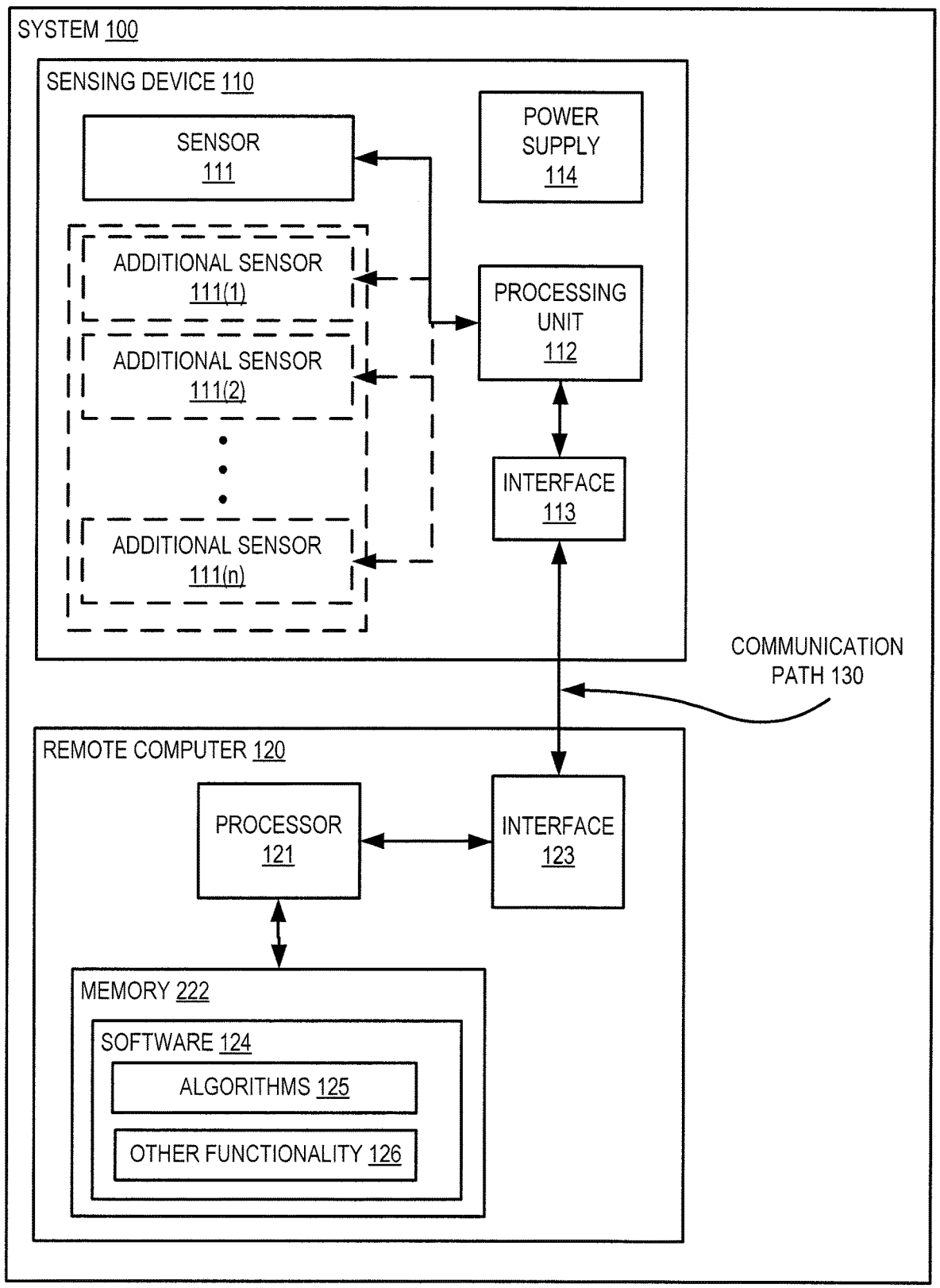
FIG. 1 illustrates one system for detecting airborne contaminants, according to an embodiment.

FIG. 1 shows a system 100 for detecting airborne contaminants. Airborne contaminants may include chemical toxins, molecules, and/or particulate matter. In this illustrated embodiment, system 100 includes a sensing device 110 that communicates with a remote computer 120 via a communication path 130. Sensing device 110 includes a sensor 111, optional additional sensors 111($i$) if multiple different airborne contaminants are to be detected, a processing unit 112, a power supply 114, and an interface 113 for communicating with remote computer 120 and/or a person (not shown in FIG. 1) in the vicinity of sensing device 110. Processing unit 112 is for example a microprocessor. Remote computer 120 is shown with a processor 121, memory 122, and an interface 123 for communicating with sensing device 110. Memory 122 stores software 124 with algorithms 125 and other functionality 126, such as reporting capability to a defined recipient. Remote computer 120 may be a standard desktop, laptop, tablet, or smartphone; it may be situated at or proximate to the customer or user, or it may reside with a service provider as, for example, a data center and/or be implemented via cloud services. Data analysis used to determine the presence and/or concentration of an airborne contaminant may be performed by processing unit 112, by remote computer 120, or by a combination of the two. Sensors 111 and 111($i$) may have different compositions for detection of different airborne contaminants, and may be replaceable by identical sensors or different sensors sensitive to other airborne contaminants without departing from the scope hereof.

Communication path 130 may be wired or wireless and may take place, for example, via Wi-Fi, cellular network, Bluetooth, radio frequency or a combination thereof. In an embodiment, sensing device 110 is a battery powered device and operates for extended periods of time, in which case a low-power communication circuit is advantageously employed.

Power supply 114 is capable of delivering required power. Certain sensing devices disclosed herein are suitable for efficient operation through conventional power sources used in portable/remote electronics, e.g., battery, solar cell, or miniature fuel cell. Other power sources that may be utilized by the disclosed sensing devices include alternative energy resources, such as a thermocouple, radio-frequency energy, electrochemical interactions, supercapacitors, and energy scavenging mechanisms. Power supply 114 may be based on a combination of power sources.

Figure 2:
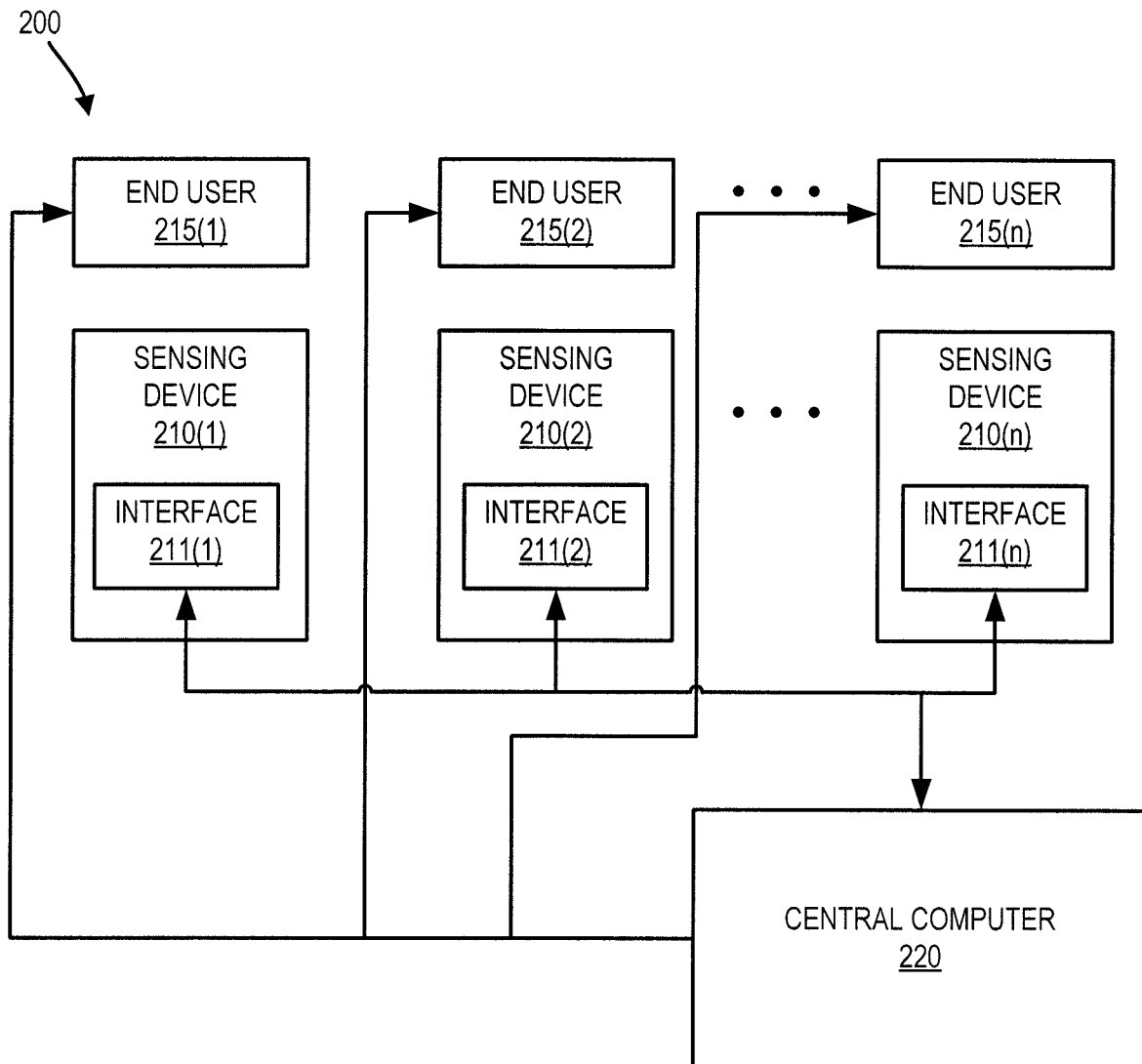
FIG. 2 illustrates one system for detecting airborne contaminants including a central computer in communication with several sensing devices, in an embodiment.

One system 200 for detecting airborne contaminants having multiple independent sensing devices 210(1) . . . 210($n$) associated with a central computer 220 is shown in FIG. 2. Each sensing device 210($i$) has an interface 211($i$) for communication with central computer 220 and is associated with an end-user 215($i$). Upon detection of an airborne contaminant by sensing device 210, central computer 220 alerts the associated end-user 215($i$). System 200 accordingly accommodates monitoring of a multitude of users all connected to central computer 220 via unique sensing devices 210($i$). Central computer 220 may be a data center hosted by a service provider and/or be implemented via cloud services. Sensors 210($i$) may have different compositions for detection of different airborne contaminants.

Figure 3:
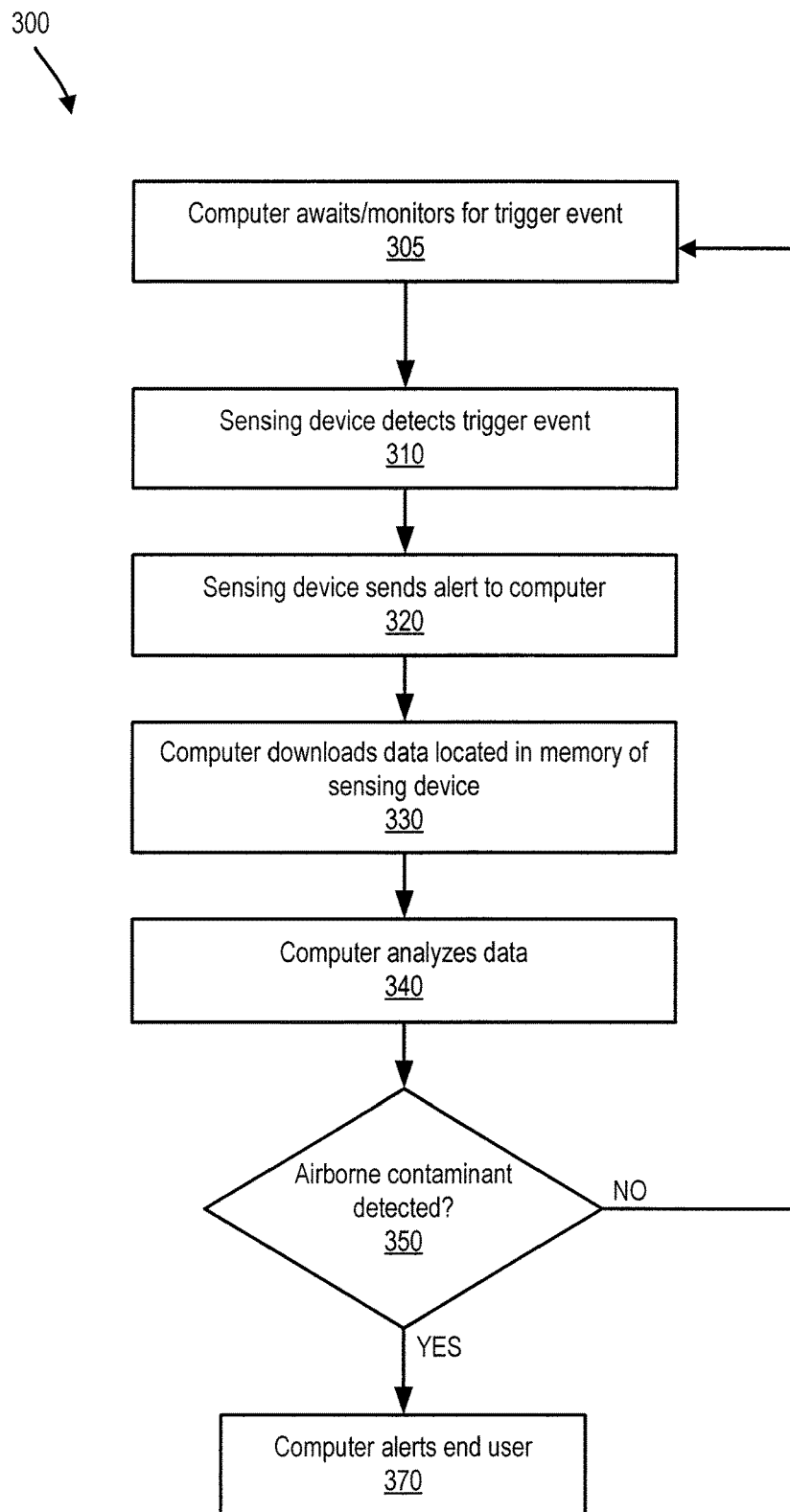
FIG. 3 illustrates one data flow method for detecting airborne contaminants, in an embodiment.

FIG. 3 illustrates one method 300 for detecting airborne contaminants. In step 305, a computer, e.g., remote computer 120 of FIG. 1, awaits or monitors for an alert from a sensing device, e.g., sensing device 110 of FIG. 1 or device 400 of FIG. 4 (discussed below). In step 310, the sensing device detects a trigger event, which is for example a measurement outside a specified range, below a specified threshold or above a specified threshold. The measurement may be a measurement of an electrical property. In step 320, the sensing device sends an alert to a computer, e.g., to remote computer 120 of FIG. 1. The computer downloads sensing data located in memory of the sensing device, e.g., in memory 122 of sensing device 110, FIG. 1, in step 330, and proceeds to analyze the data using, e.g., algorithms 125 of FIG. 1, in step 340. The sensed data may include recorded measurements as a function of time. The computer may download all data stored in the memory of the sensing device or download only portions of the data deemed necessary and/or interesting by the computer. Following the analysis in step 340, a decision 350 is made whether or not the trigger event was associated with the detection of an airborne contaminant. If NO, the computer returns 360 to step 305. If the answer is YES, the computer alerts 370 the end-user via suitable forms of communication. For example, an email or text message may be sent to the end-user, a phone call may be placed to the user, or, if the computer is located at the end-user, a message may be displayed on the screen optionally in conjunction with an audible cue or tactile alarm such as vibration. The alert may be accompanied by further details including but not limited to the type of airborne contaminant(s) detected, the concentration(s), the time of detection, and the sensing device ID and location.

Figure 4:
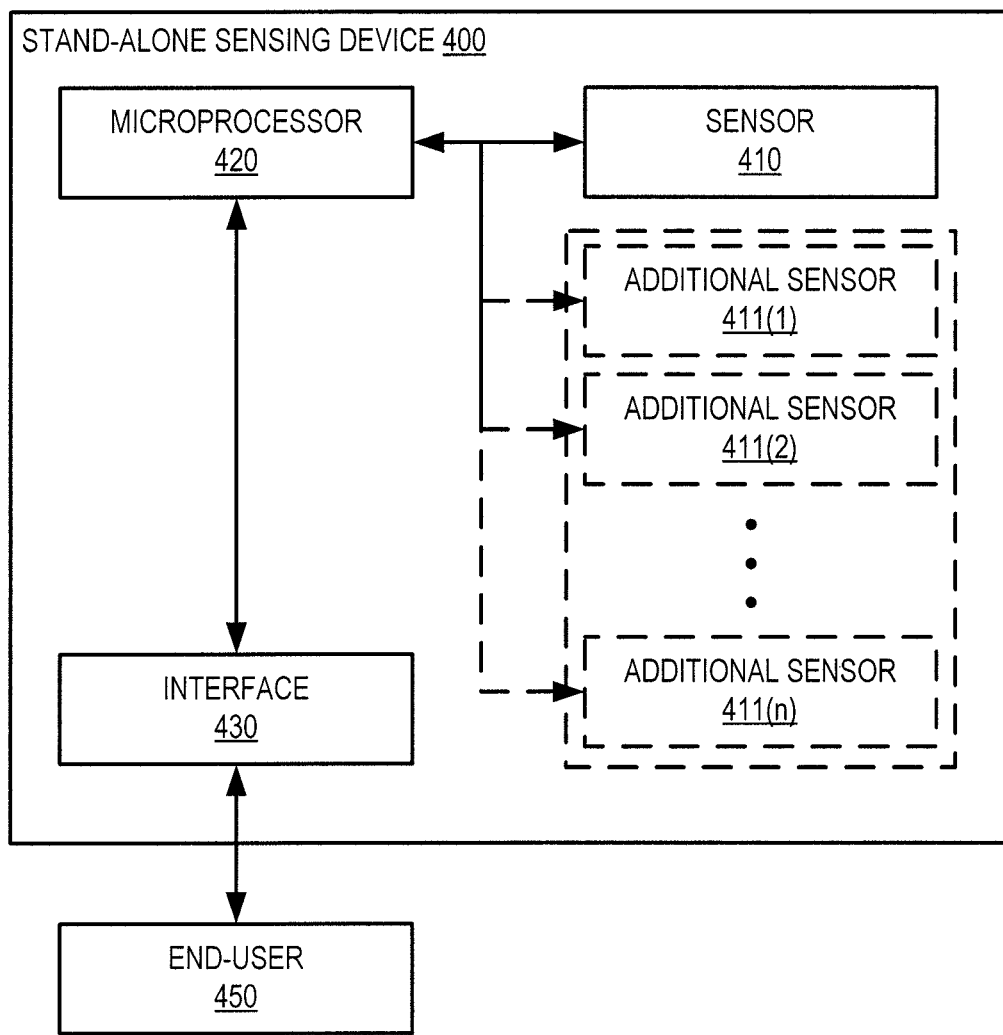
FIG. 4 illustrates one standalone device for detecting airborne contaminants, including full onboard analysis and reporting capability, in an embodiment.

A stand-alone sensing device 400 for detection of airborne contaminants is shown in FIG. 4. Device 400 is a fully integrated solution with onboard analysis and reporting capability. Stand-alone sensing device 400 includes at least one sensor 410, optional additional sensors 411($i$) (of different compositions and/or for different contaminants), a microprocessor 420 and an interface 430 for communicating with an end-user 450. Sensors 410, 411($i$) are sensitive to airborne contaminants and generate signals that are processed and analyzed by microprocessor 420. Upon detection of an airborne contaminant, sensing device 400 alerts end-user 450 via interface 430. The alert may include audible, visible, and/or tactile cues generated directly by device 400, which is suitable when the end-user is close to device 400 (e.g., when a sensing device 400 is worn on the body of the end-user or located in a home or room similar to a fire alarm). In an embodiment, sensing device 400 is controllable by end-user 450 via interface 430.

The systems illustrated in FIGS. 1, 2, and 4, and the method of FIG. 3, are capable of providing real-time monitoring of airborne contaminants and real-time feedback to an end-user. In some use scenarios, a sensing device, e.g., one of the sensing devices in FIGS. 1-4, monitors airborne contaminants in real-time but does not provide real-time feedback. For instance, if the sensing device does not have full onboard analysis and/or reporting capability and is not in communication with a computer having those capabilities, real-time data may be stored onboard the sensing device for readout when convenient. In an embodiment, the sensing device includes a removable memory (e.g., memory 630, FIG. 6) readable by a standard computer. The removable memory may be, for instance, an SD card, a USB stick, or other computer-readable media. In another embodiment, data stored in the onboard memory may be read by a computer interfacing with the device utilizing a computer interface port such as USB, Firewire, Bluetooth or Ethernet.

Figure 5:
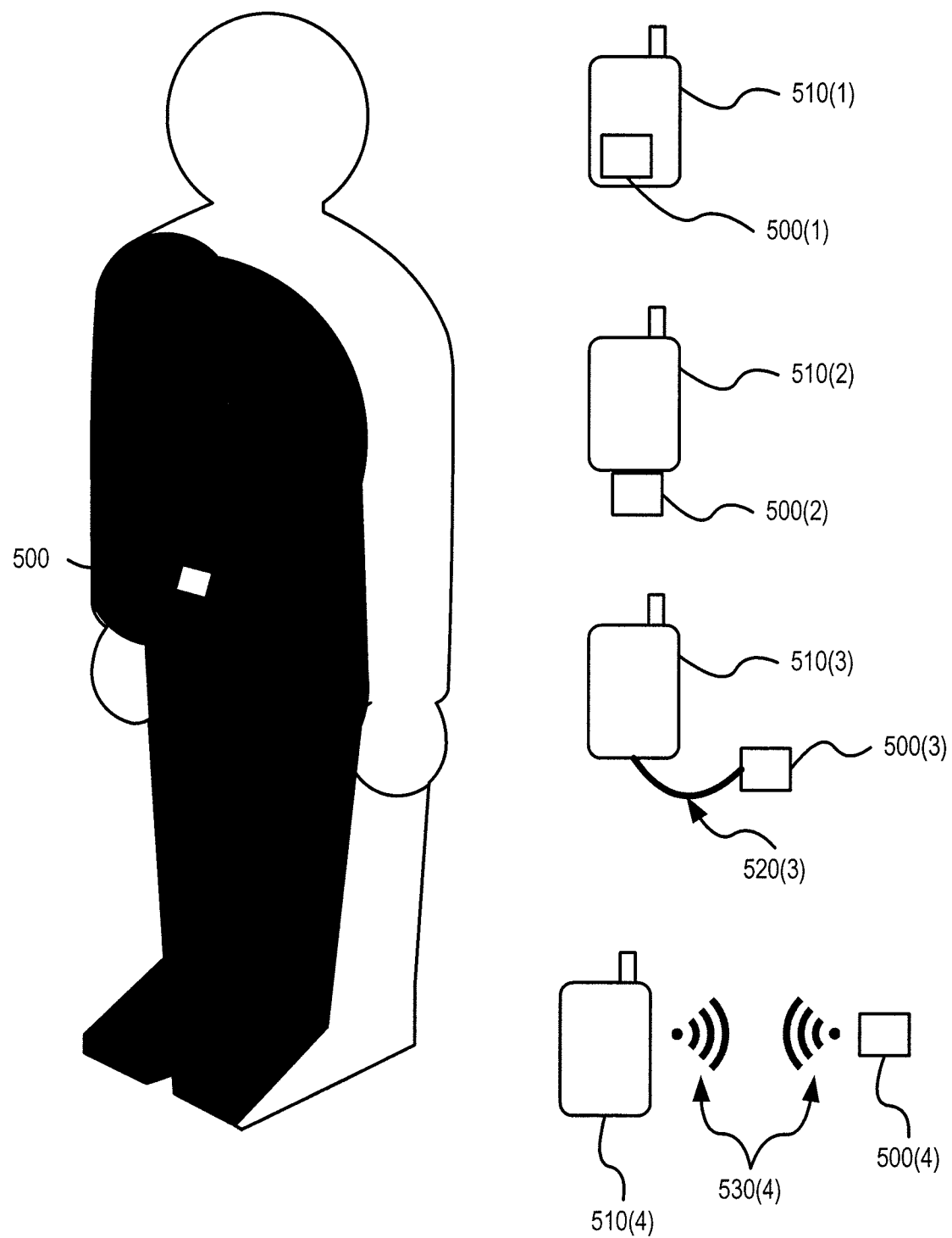
FIG. 5 shows one mobile sensing device for detecting airborne contaminants, in an embodiment.

The sensing devices disclosed herein are preferably small (personnel badge sized), easy to read, and simple to operate (e.g., wherein a laboratory analysis is not needed). The sensors target specific contaminants and, by using multiple sensors, a number of contaminants can be simultaneously detected by a single sensing device. The sensing devices may be wall-mountable or wearable and have applications, for example, in medical centers to monitor the environment of pediatric (and other) patients, in supposedly smoke-free environments such as hotel rooms and rental cars to measure tobacco smoke contamination, and in manufacturing facilities utilizing materials or processes capable of generating hazardous vapors. FIG. 5 illustrates one wearable, personal sensing device 500. Sensing device 500 may be configured with a cell phone or other personal device. FIG. 5 illustrates several examples of a sensing device being configured with a cell phone: Sensing device 500(1) is integrated in cell phone 510(1), sensing device 500(2) is directly connected to cell phone 510(2), sensing device 500(3) is connected to cell phone 510(3) via connector 520(3), and sensing device 500(4) is in wireless communication (530(4)) with cell phone 510(4). When sensing devices 500, as exemplified by sensing devices 500($i$), is configured with a cell phone, sensing device 500 may, at least in part, utilize the processor, memory, power supply, and/or interface of the cell phone. Since a specific sensor in a sensing device may be readily replaced to monitor a different airborne contaminant, and the sensing device may further contain multiple different sensors, sensing device 500 may be adapted to detect an array of different molecules or hazardous vapors. The specific airborne contaminants detectable by sensing device 500 (and other devices disclosed herein) include, but are not limited to, carbon monoxide (CO), nicotine, 4-(methylnitrosamino)-1-(3-pyridyl)-1-butanone (NNK), acetaldehyde, and formaldehyde. In an embodiment, sensing device 500 includes sensors and/or sensing materials of different compositions for simultaneous detection of multiple airborne contaminants.

Figure 6:
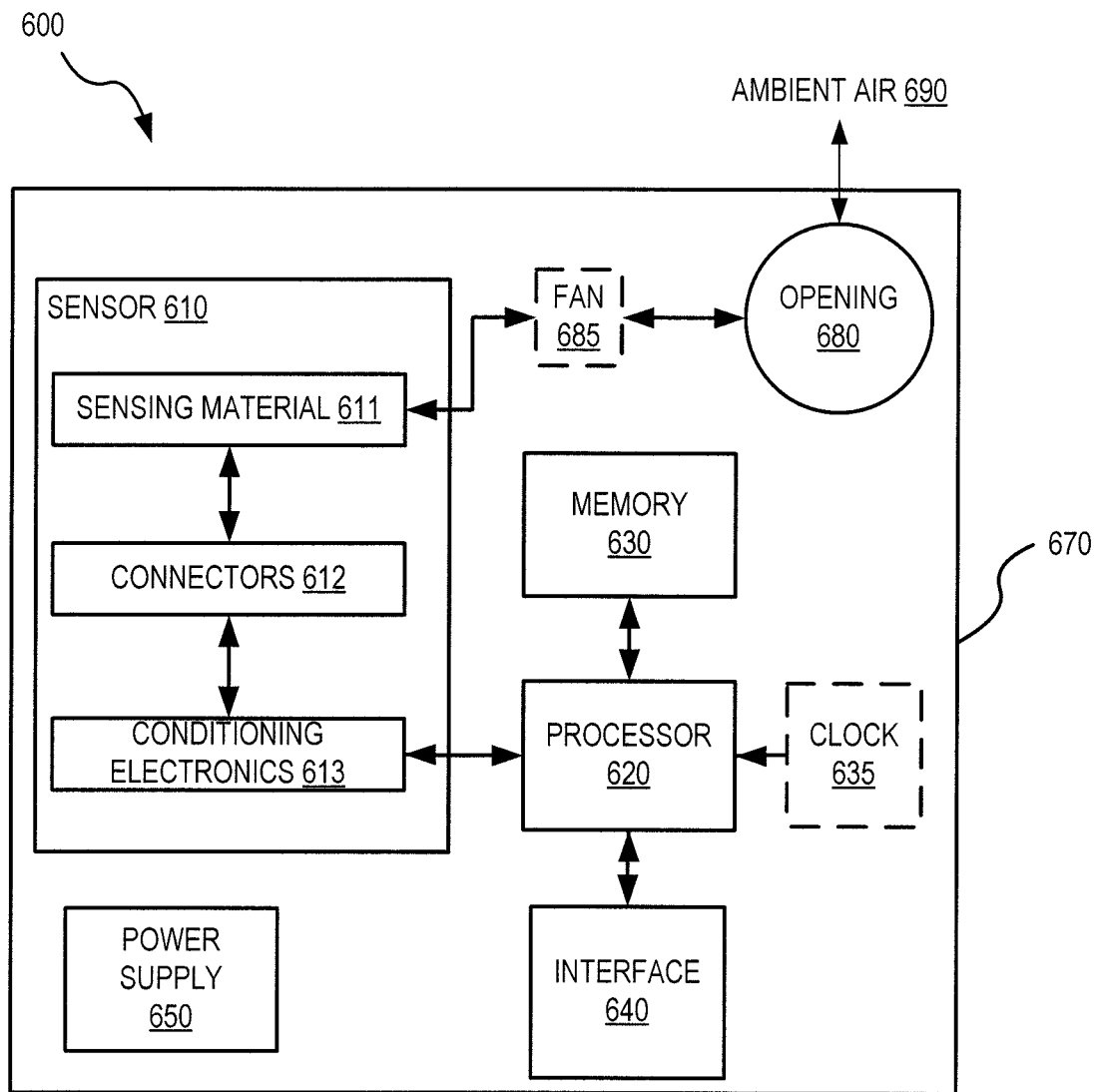
FIG. 6 illustrates one sensing device for detecting airborne contaminants, in an embodiment.

FIG. 6 illustrates one sensing device 600 for detection of airborne contaminants. A sensor 610 includes a sensing material 611 sensitive to an airborne contaminant, connectors 612, and conditioning electronics 613. Conditioning electronics 613 interrogate sensing material 611 via connectors 612 and generate signals that correlate to the presence, concentration, and/or a change in concentration of an airborne contaminant. The specific metric used to determine the presence, concentration, and/or change in concentration may be a single measured property. Alternatively, or in addition, the metric may be a combination of several properties, a relationship between several properties, the variation of one or more properties over time, or the dependence of one or more properties as a function of one or more conditions applied by conditioning electronics 613, such as described below. In an embodiment, sensing material 611 may have multiple compositions for detection of multiple airborne contaminants, each composition being sensitive to a different airborne contaminant. Conditioning electronics 613 may interrogate different properties of each of the multiple compositions and different metrics may be applied to determine the presence, concentration and/or change in concentration of each of the multiple different airborne contaminants.

Sensing device 600 includes a processor 620, for processing of signals generated by conditioning electronics 613, and a memory 630, for storing measurements and data generated by processor 620 and instructions used by processor 620. Also included in sensing device 600 is an interface 640, for communicating with a remote computer and/or a person in the vicinity of sensing device 600, and a power supply 650. Optionally, sensing device 600 includes a clock 635 for time-stamping measurements stored to memory 630. This is useful if sensing device 600 does not have full onboard analysis and/or reporting capability or is not in communication with a computer having those abilities. For example, sensing device 600 may be placed in a non-smoking rental car to monitor tobacco smoking so that time-stamped measurements/results (e.g., results stamped with a date and time of sensing) may be read out upon return of the rental car.

Although sensing device 600 may operate unenclosed, it is in many likely scenarios advantageous to provide an enclosure 670 having an opening 680, such that sensing material 611 is in contact with ambient air 690, while other components of sensing device 600 remain protected. Optionally, sensing device 600 includes a fan 685 that forces flow of ambient air 690 over sensing material 611.

Sensing device 600 may be incorporated in a variety of sensing systems, for example systems 100 (FIG. 1) and 200 (FIG. 2) as sensing device 110 and 210, or sensing device 600 may serve as sensing device 400 (FIG. 4) or 500 (FIG. 5). The functionality incorporated in processor 620, memory 630, and interface 640 may be tailored to suit a given implementation. As an example, in the case of the fully integrated stand-alone sensing device 400 of FIG. 4, memory 630 may store software instructions for data analysis and reporting, including algorithms and analysis parameters such as thresholds.

Exemplary embodiments of sensor 610 are disclosed below and utilize polymer films as sensing material 611. In these embodiments, a measurable change in electrical properties of the sensing material results from binding of airborne contaminants to the polymer film. Conditioning electronics 613 may measure suitable electrical properties of sensing material 611, for example, resistance, conductivity, current, voltage, capacitance, transistor on current, transistor off current, and/or transistor threshold voltage. In one embodiment, sensing material 611 is a conductive polymer and the airborne contaminant acts as a dopant or dopant-depletion agent such that adsorption of airborne contaminant onto sensing material 611 results in a change in conductivity. Conductive polymers may be π electron-conjugated conductive polymers; for example, polyaniline or a derivative thereof, polypyrrole or a derivative thereof, polythiophene or a derivative thereof, or a copolymer of two or more kinds of these materials are suitable conductive polymers.

In an embodiment, sensing material 611 is a thin film. A thin film, as opposed to a thicker substrate, has a greater surface area to bulk volume ratio. Hence, thin films optimize the density and availability of protonated receptor sites by minimizing the diffusion distance necessary for the adsorbant, e.g., an airborne contaminant, to travel during binding events. Thin films also increase responsivity if the reporting electrode lies beneath the polymer film. Hence, a thin film sensing material exhibits a relatively fast response to the occurrence of airborne contaminants, which makes thin films particularly suitable for real time detection sensing devices such as disclosed herein. The various techniques for creating these thin films include electropolymerization, spin casting, and laser deposition. Thin films of the disclosed sensing devices may be produced by any conventional method. However, the ability to control the thickness and formulate the films in an environment typical of printed circuit production is an important feature of film production. Thus, in preferred embodiments, the thin films are produced by phase inversion-spin coating onto a suitable substrate.

The substrate of the thin film may be rigid or flexible material, conducting, semiconducting, or dielectric. The substrate may be a monolithic structure, or a multilayer or other composite structure having constituents of different properties and compositions. Suitable substrate materials include quartz, glass, alumina, mica, silicon, III-V semiconductor compounds, and other materials. Optionally, additional electronic elements may be integrated into the substrate for various purposes, such as thermistors, integrated circuit elements or other elements.

In an embodiment, sensing material 611 is molecularly imprinted, through a process by which guest or host molecules (functional monomers or polymers) self-assemble around a molecular template, thereby forming a recognition element with binding sites corresponding to functional groups in the template molecule. The recognition elements form a binding cavity which is cross-linked into a matrix. The template molecule is removed, leaving behind a molecularly imprinted polymer complementary in shape and functionality to the template molecule, which then rebinds chemical targets identical to the original molecular template. Molecular imprinting may also be achieved by a synthetic process utilizing monomers. The wet phase inversion procedure (Wang, et al. (1997) *Langmuir* 13:5396; Shibata, et al. (1999) *J. Appl. Poly. Sci.* 75:1546; Trotta, et al. (2002) *J. Membr. Sci.* 201:77) for preparation of molecularly imprinted polymers involves a polymerized starting material dissolved with the template in a theta solvent. A template-host network is allowed to form in solution and precipitated by immersion in a non-solvent. This procedure may be adapted to the production of thin, 300 nm to 5 m, films via spin coating (see, e.g., Crabb, et al. (2002) *J. Appl. Polym. Sci.* 86:3611; Richter, et al. (2006) *J. Appl. Polym. Sci.* 101:2919; Campbell, et al. (2009) *Surface and Interface Analysis* 41:347, each incorporated herein by reference) and hydrogen bond interactions between the template and host polymer, allowing for the manufacture of molecularly imprinted polymer thin films as sensing material 611.

As previously noted with respect to devices 110, 210 and 400, sensing device 600 may contain multiple sensors (not shown in FIG. 6) for detection of multiple different airborne contaminants. Such a multiplexed device may incorporate multiple sensors for detection of unrelated airborne contaminants or for detection of airborne contaminants from the same source. In the former case, multiplexing serves to provide versatility and may for instance be able to detect both cigarette smoke and a house fire. In the latter case, multiplexing may serve to improve the sensitivity of the sensing device or more reliably and accurately identify the source of an airborne contaminant. For instance, formaldehyde is an airborne contaminant that may be result from outgassing from certain glues. Due to its hazardous nature, monitoring of formaldehyde contamination in the air may be beneficial in manufacturing facilities utilizing such glues. However, formaldehyde is also a by-product of cigarette smoking and a sensing device capable of detecting nicotine and formaldehyde may determine if the formaldehyde contamination is caused by manufacturing materials, e.g., glue, or by a worker smoking a cigarette.

Examples of Sensing Devices

This section is divided into the following subsections: Protonated Conductive Polymer; Composite Polymer with Protonated Conductive Component and Targeting Additive; and Dielectric Polymer.

Protonated Conductive Polymer

Figure 7:
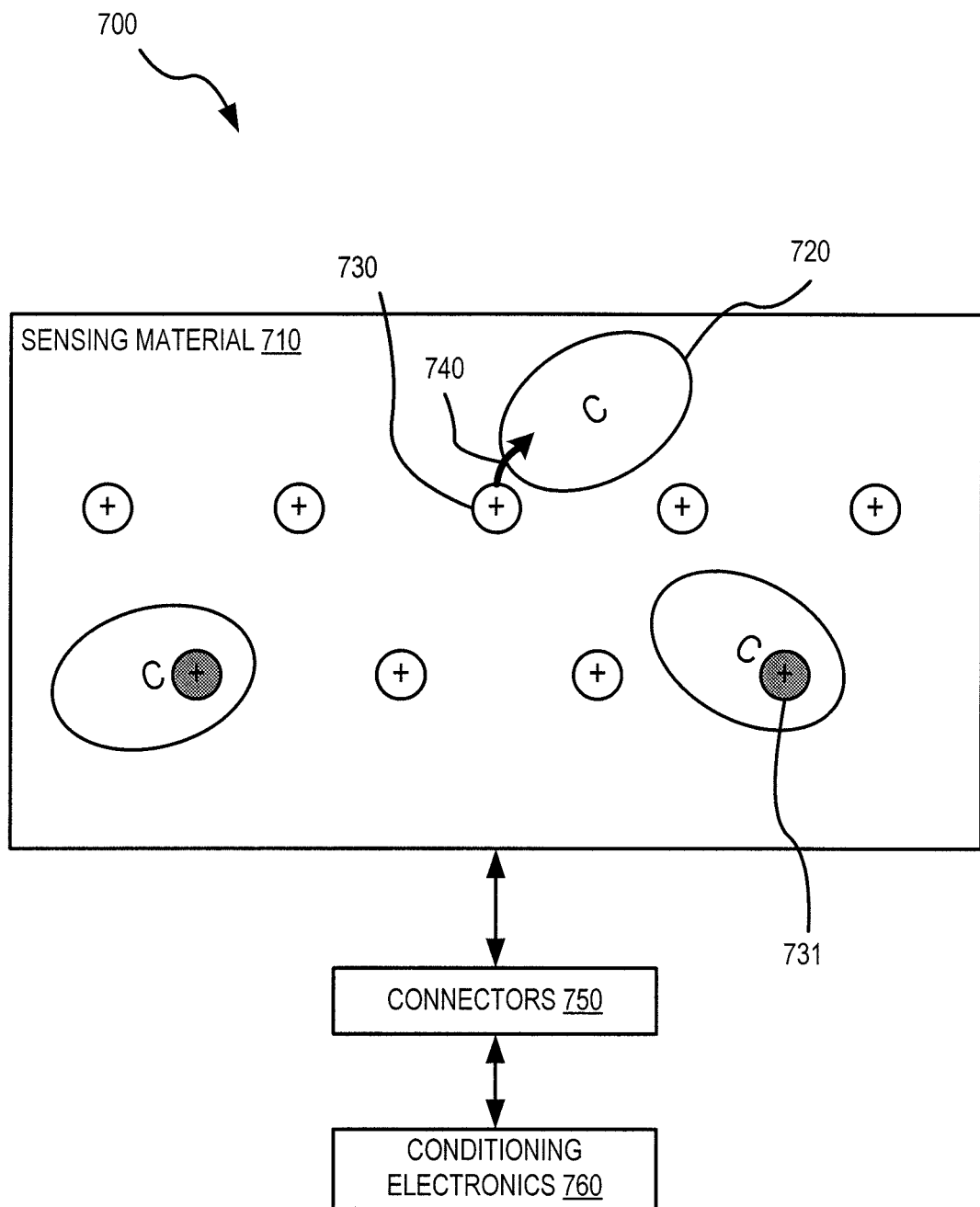
FIG. 7 illustrates an embodiment of a sensing device, based on a protonated, electrically conductive polymer, for detection of airborne contaminants.

In a sensing device 700 illustrated in FIG. 7, a sensing material 710 (e.g., sensing material 611 of FIG. 6) is a protonated, electrically conductive polymer with a binding affinity for an airborne contaminant of interest 720. Upon binding of airborne contaminant 720 with sensing material 710, airborne contaminant 720 takes up a proton 730 from sensing material 710, thereby deprotonating sensing material 710. Sensing material 710 is interrogated (e.g., conditioning electronics 613 of FIG. 6) by conditioning electronics 760 via connectors 750 (e.g., connectors 612 of FIG. 6). The loss of proton 730 to airborne contaminant 720 (process indicated by arrow 740; proton lost to airborne contaminant 720 labeled 731) leads to a change in the electrical properties of sensing material 710, which is measured by conditioning electronics 760. The electrical property measured by conditioning electronics 760 may be one or more of, for example, resistance, conductivity, current, voltage, or capacitance, and may be measured as a function of a condition applied by conditioning electronics 760. Deprotonation may be detected by measuring a corresponding resistance increase or conductivity decrease. Increased sensitivity and/or specificity of sensing device 700 is for example achieved by molecularly imprinting sensing material 710. Examples below disclose embodiments of sensing device 700 with (Example II) and without (Example I) the use of molecular imprinting.

Examples of electrically conductive polymers suitable as sensing material 710 include, but are not limited to, polyaniline and polycarbozole.

Example I

Nicotine Detection Using Protonated, Conductive Polymer

This example illustrates a specific embodiment of sensing device 700 of FIG. 7, in which nicotine is detected using a protonated, conductive polymer film. This device may serve to monitor and detect second- or third-hand cigarette smoke. Sensing material 710 of FIG. 7 is in this case a film of doped, electrically conductive polyaniline (PANi).

As a sensor for nicotine, the key element of doped, electrically conductive PANi is the presence of protonated nitrogen atoms that give up a proton to nicotine, a base, which is adsorbed to the film from the nascent vapor. Measurement using conductive polymer films is performed either by coating the surface of an electrode with the doped polymer and measuring electrical changes with reference to a redox electrode or by making a true planar chemiresistive structure. The latter may be used with a variety of conductive polymers, may be designed to create a higher value of resistance, and has potential for rapid measurements with small, personal-sized devices. This example discloses a planar chemiresistive sensor that reports on exposure to secondhand smoke from ambient nicotine concentrations in real time. This allows for demonstration of changes in air nicotine from a specific smoking event.

Materials and Methods.

Polyaniline was purchased from Polysciences, Inc. as the undoped emeraldine base form with a molecular weight of 15,000 and a conductivity of $10^{-10}$ S/cm. Formic acid, >98%, was purchased from EMD Chemicals and used to dissolve the polyaniline prior to spin casting. Secondary doping increased the sensitivity of the films and HCl, purchased from Fisher Scientific (ACS Certified), was used in a 1.0 M aqueous solution. For laboratory studies, nicotine purchased from Alfa-Aesor, 99%, was used. All reagents were used as received without further treatment. The standard cigarettes used in the smoking chamber were 3RF4 reference cigarettes, containing ~0.8 mg of nicotine.

The polymer films for detecting nicotine were spin-cast polyaniline. Polyaniline, which in its conductive form is insoluble. However, the emeraldine base may be dissolved in several solvents including the 98% formic acid used herein. The spin casting solution was produced from formic acid as a 1% (by weight) polymer solution. Because the $pK_a$ of formic acid is 3.77, polyaniline in this solution was 50% protonated; the amine and imine nitrogen atoms had different $pK_a$ values. To complete the protonation process and increase the sensitivity of the film, secondary protonation in 1.0 M HCl was employed. Protonated solutions are green while solutions of the base are deep blue. Morphology and roughness were investigated by atomic force microscopy using a Pacific Nanotechnology Nano-1 microscope in close contact mode.

Figure 8:
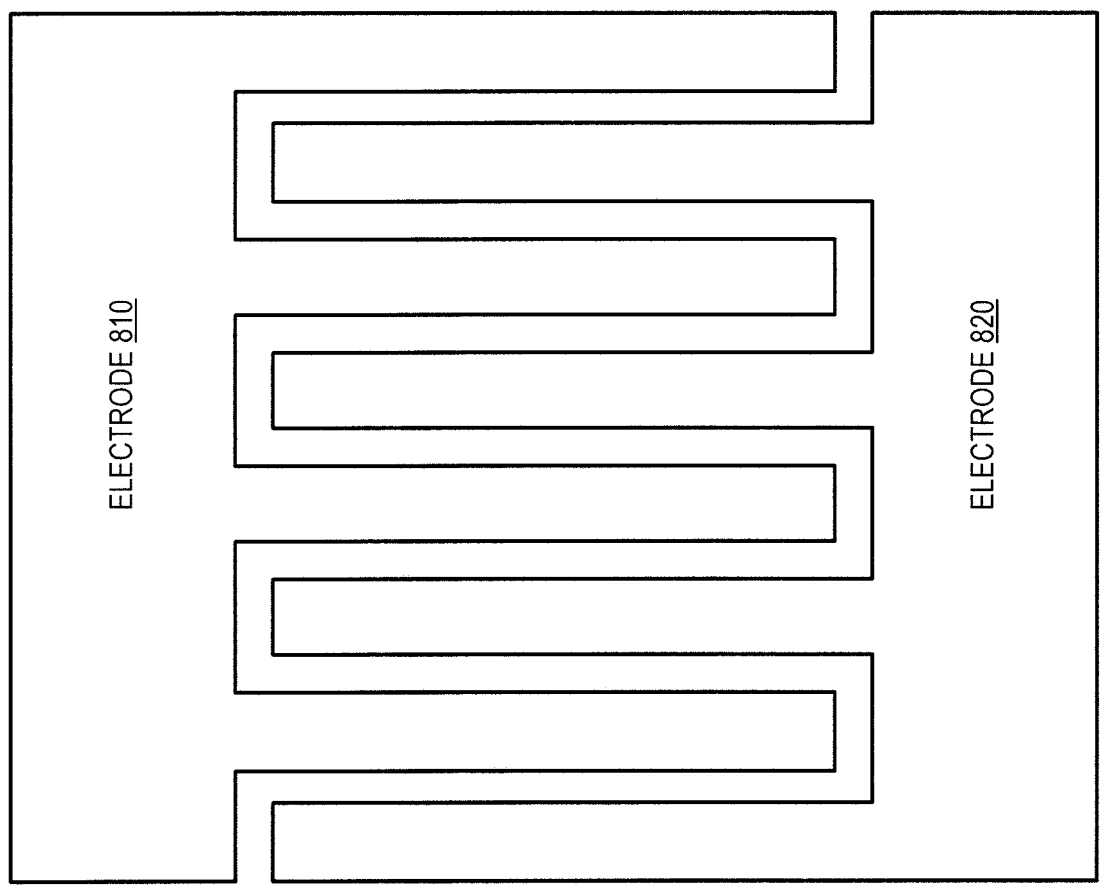
FIG. 8 illustrates an interdigitated electrode pattern used in resistance-based sensing devices for detecting airborne contaminants, in an embodiment.

The conductive sensors were constructed on oxidized silicon substrates using chromium metal with a nickel overlayer for the electrode and the protonated polyaniline film as the active element above the electrode. The electrode was patterned into an interdigitated grid with 40 μm fingers and 20 μm spacing. This electrode configuration is illustrated schematically in FIG. 8 with electrodes 810 and 820.

Prime grade silicon wafers with a 5000 Å thermally deposited oxide layer were used for the substrate. These films were patterned by photolithography and subsequently wet-etched to produce the final electrodes with a total area of 376 $mm^2$, following vapor deposition of 200 Å of chromium and a 1000 Å overlayer of nickel. Liftoff was accomplished using acetone, with final rinses of water.

Subsequently, the polyaniline polymer layer was spun on the sample. An aliquot of 0.5 ml of solution was dropped onto the substrate (oxidized silicon), and allowed to spread for 20 seconds. The spin-coater was then brought up to 4000 rpm for 30 seconds. This resulted in deposition of films with a typical thickness of approximately 100 nm. In the final step, secondary doping with 1.0 M HCl was accomplished by dip-coating for 30 seconds. After this treatment, background (washed) resistance values were measured, and the sensor was ready for use in binding studies.

Smoking machine experiments were carried out in a Teague Enterprises package (Teague Enterprises, Davis, Calif.), composed of a TE-10 smoking system and a mouse exposure system. The smoking device was microprocessor controlled and produced both mainstream and sidestream (separately or simultaneously) smoke from filtered research cigarettes produced with controlled nicotine content. Up to ten cigarettes could be smoked simultaneously following the Federal Trade Commission procedure and expended cigarettes could be automatically extinguished and ejected. Smoke was captured and transferred to a mixing chamber for exposure experiments; sidestream or mainstream smoke was mixed with air and then passed into the exposure chamber. However, for the experiments described here, the system including sample lighting and extinguishing was operated in manual mode. A filter was available for venting and purging. The exposure chamber was calibrated for total suspended particles (TSP), carbon monoxide and nicotine concentration determined for selected mixing valve and fan settings. All measurements using the Teague Enterprises system were made with the polymer sensors in the exposure box, using calibrated operational parameters.

The laboratory sample system was composed of a small nylon box, containing spring-mounted electrodes and a small (~3 $cm^3$) well filled via a syringe through a septum. The sensor assembly was placed on the electrodes above the well and a nylon cap was attached using a torque wrench to ensure reproducible pressure of the sensor against the spring-mounted electrodes. Nicotine (1 mL) was injected into the well and the response of the sensor was recorded. To follow the recovery of the sensor after exposure to nicotine, dry nitrogen was passed through the well to evaporate the nicotine. In both experimental chambers, the change in the resistance of the sensor was measured using a multimeter connected to a laboratory computer.

The resistance, R, of the polymer sensor was measured using a Keithley Model 2100 6½ Digit Multimeter. During the measurement, constant current of 1 mA was applied and the voltage through the film was recorded, providing a resistance value via Ohm's law. Total dissipated power within the sensor was less than 0.5 W. Four point measurements were found unnecessary and all of the reported data were obtained using two contacts. Data were taken at a rate of 1 Hz over as long as 9 hours, but typically over considerably shorter times. The resistance increased from its low background value prior to exposure, typically 600Ω, through to a plateau, associated with the level of nicotine in the sample chamber. Data are reported as normalized resistance, referenced to an initial, out of chamber background value.

Films were exposed to analyte concentrations that ensure a challenge to the adsorption process. The results provided an indication that the shift in the resistance value and the rate of change in the resistance, were proportional to the quantity and identity of the analyte adsorbed.

Results and Discussion.

The morphology of the film surface was investigated by atomic force microscopy (AFM) of films produced on both silicon oxide and glass under the coating conditions described above. The undoped film was rougher than the doped material and more irregular with surface defects. The doped film was somewhat smoother and the minimal occurrence of surface defects provided an ideal material for adsorption of the target molecule from the vapor phase.

The physical property associated with the target molecule presence in the film was the increase in the resistance. Sensor functionality depended upon detecting differences in this property as a function of the adsorption of the target nicotine onto the sensor chip. Numerous films were tested using both pure nicotine in the small lab-built chamber and nicotine emitted from cigarette consumption as measured in the Teague smoking system. Data presented here are typical of these observations.

Testing of the sensor in the laboratory chamber indicated that injection of nicotine into the sample well evoked an immediate rise in measured resistance. Nicotine vapor pressure was quite small at room temperature, so a series of experiments, injecting nicotine at different initial temperatures (providing different vapor pressures and, hence, vapor phase concentrations of nicotine in air) and recording the resistance was completed. The relationship of nicotine vapor pressure to sample temperature is well established and was used in this analysis (Young & Nelson (1928) *Ind. Eng.*

Figure 9:
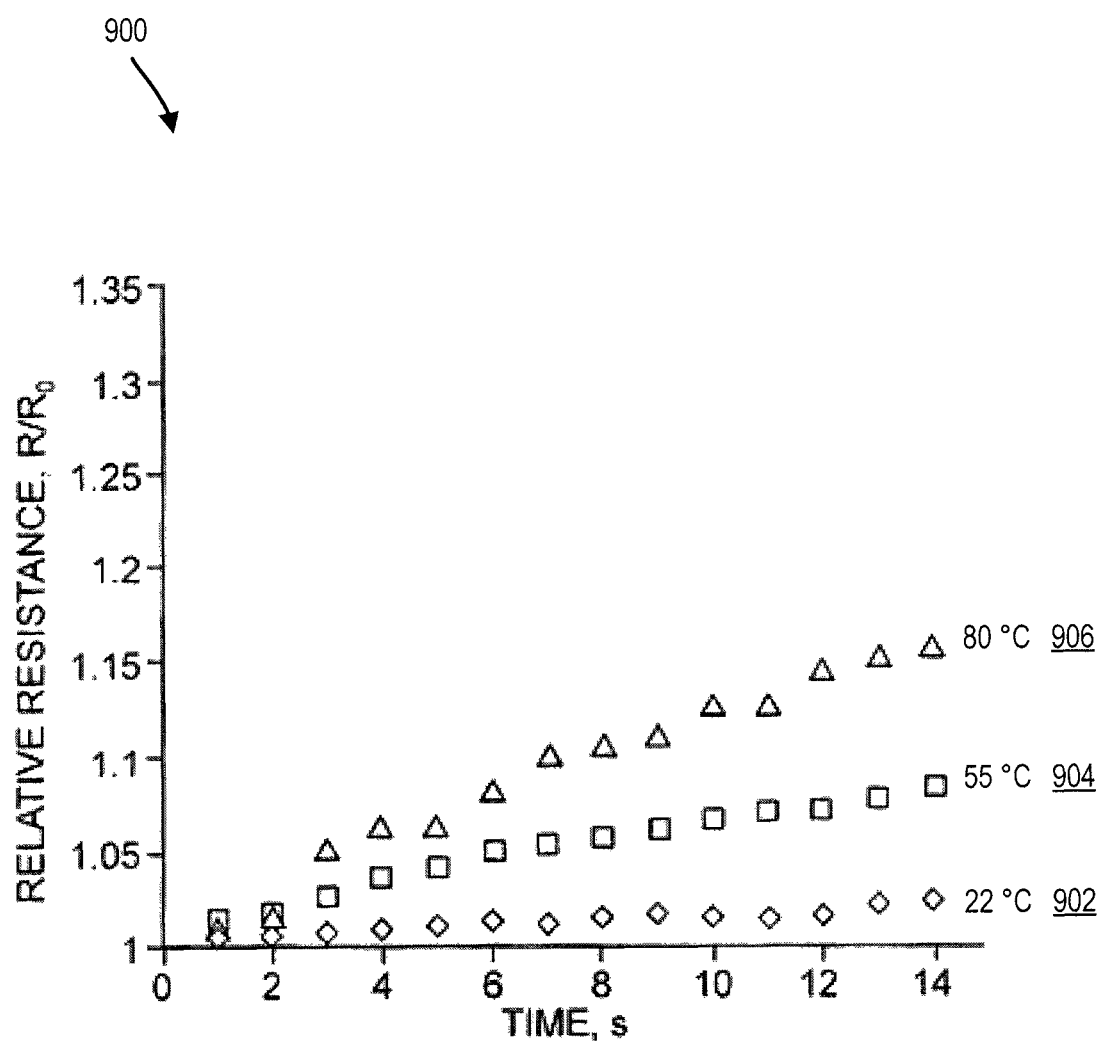
FIG. 9 shows the response of a sensing device, exemplary of the sensing device of FIG. 7, to nicotine vapor.
Figure 10:
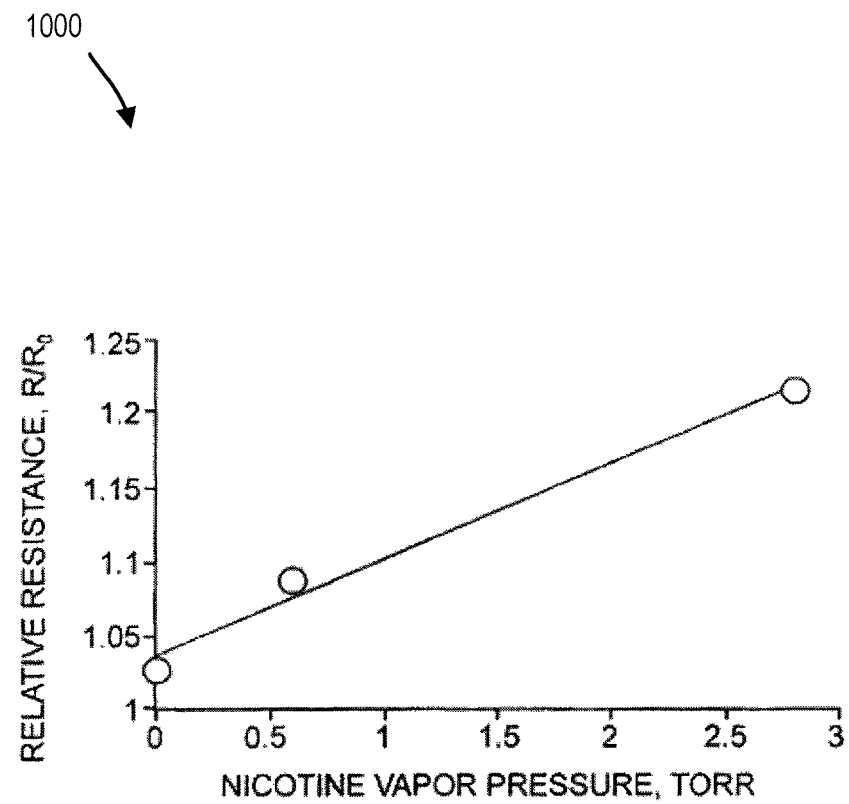
FIG. 10 illustrates a relation between sensor response and nicotine vapor pressure for a sensing device exemplary of the sensing device of FIG. 7.

Chem. 20:1381-1382). The results of this study are shown on plot 900 of FIG. 9 for three different nominal temperatures, 22° C. (data 902), 55° C. (data 904), and 80° C. (data 906). For example, consider the film response to the injection of nicotine at a nominal 80° C. The rise of the signal as the sample was injected and the beginning of a plateau of the signal (and slight decrease) as the sample cooled was clearly demonstrated. FIG. 10 shows a plot 1000 of the signal (15 seconds post injection) as a function of the nicotine vapor pressure at the nominal temperatures. A linear fit to the data with a correlation coefficient of 0.99 is shown. The nicotine began to cool almost immediately, therefore, deviation of the fit from an exact correlation with temperature was to be expected. The absence of constant temperature capability in this device precluded its use as a calibration system. However, the trend of increasing resistance with increasing temperature was clear and demonstrated the responsiveness of the film to pure nicotine. The nicotine concentrations in this device were estimated to be of the order of a few ppm.

Figure 11:
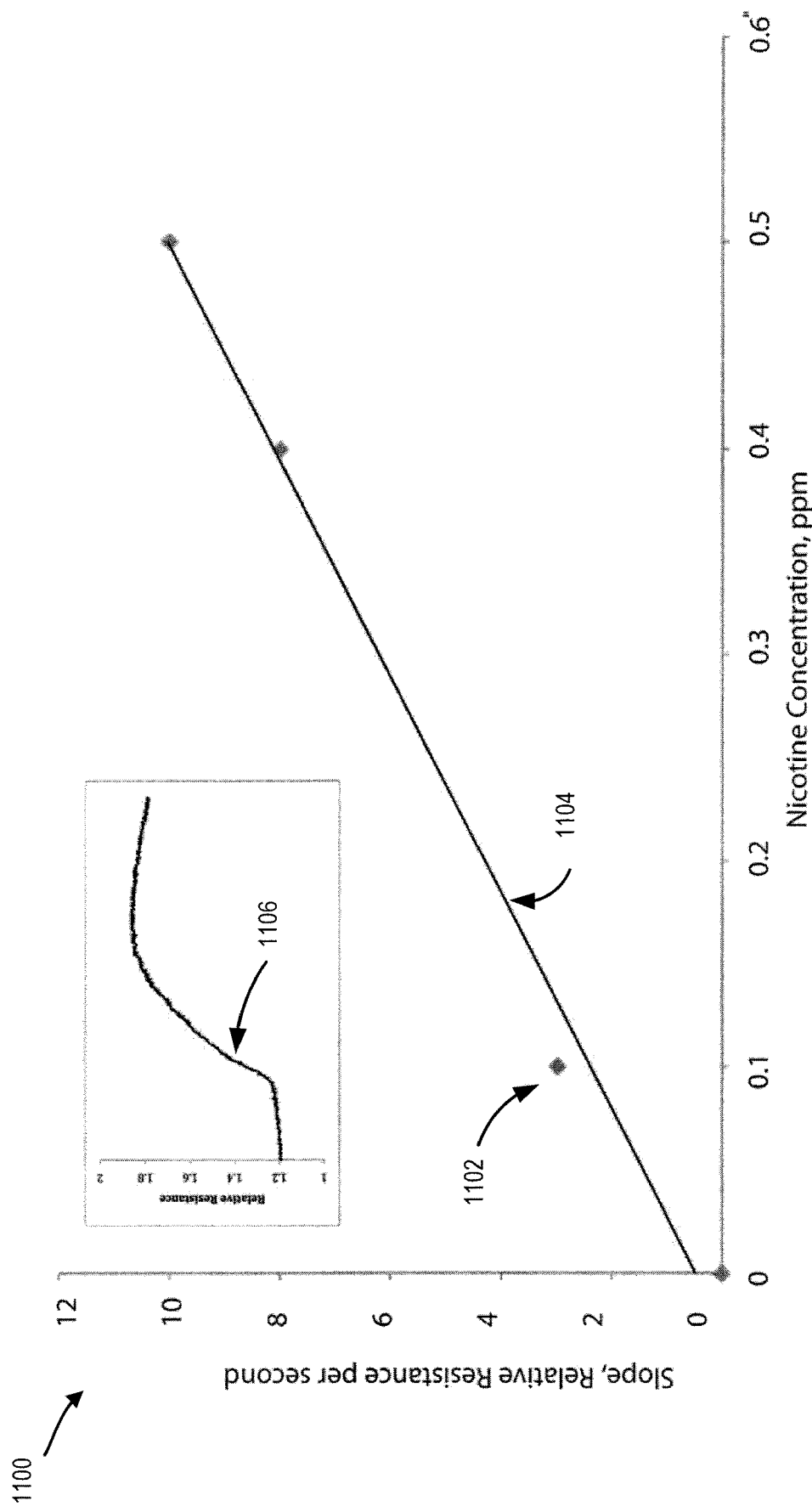
FIG. 11 shows a calibration curve for a nicotine sensing device exemplary of the sensing device of FIG. 7.

The data laid out in plot 1100, FIG. 11 provide a calibration of the rate of relative resistance change as a function of parts per billion (ppb) of nicotine in air. The measurements shown were reproducible to within 5%. The data (1102) are fit via linear regression (1104) with a slope of $1.90 \times 10^{-6} \Omega_{rel} s^{-1}$ $ppb^{-1}$ and a correlation coefficient of 0.99. The slopes (for example slope 1106) are a preferred measure of the concentration; use of absolute resistance changes is problematic since the sensor resistance will continually increase if nicotine remains present in the ambient atmosphere. This calibration is intended for use in reporting sensor data in terms of ppb of nicotine rather than as a function of cigarette exposure.

Figure 12:
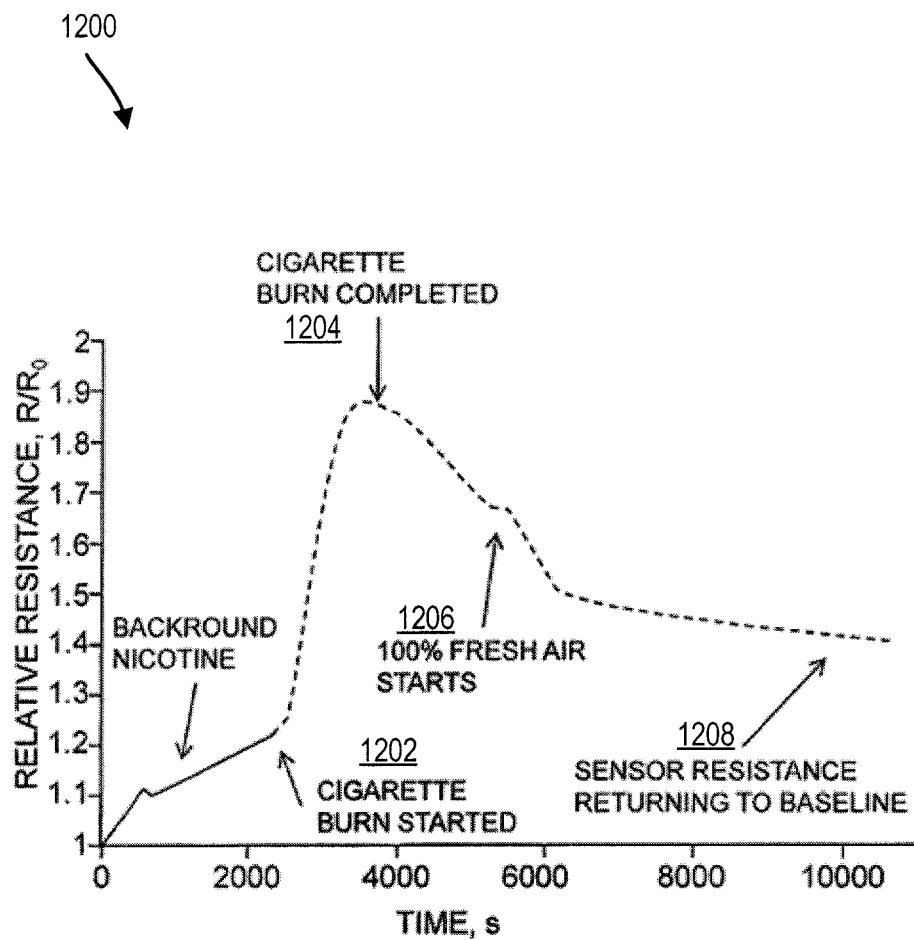
FIG. 12 shows the time evolution of the response of a nicotine sensing device, exemplary of the sensing device of FIG. 7, exposed to smoke from a single cigarette followed by fresh air.

Graph 1200 of FIG. 12 shows the time evolution of the sensor film signal for smoking a single cigarette in the Teague system. During the smoking process, sidestream smoke was fed into the exposure chamber and the resistance increased as long as the smoking continued, indicating continued adsorption of nicotine into the film (between points 1202 and 1204). The signal stopped increasing as the cigarette was extinguished at point 1204 and decreased slowly because air entering into the exposure chamber from the smoking system contained no additional nicotine. After approximately 6 min, the chamber was purged with 100% fresh (room) air (point 1206) and the sensor resistance dropped to a level approximately 20% above the chamber background (points 1206 to 1208). The initial slope of the signal was determined to be $8.73 \times 10^{-4} \Omega_{rel} s^{-1}$, indicating, from the calibration curve in FIG. 11, a nicotine level of 450 ppb for this exposure. The system calibration at the inflow/outflow settings of the exposure chamber provides that the dynamic nicotine concentration in this situation from the cigarette consumption alone was 0.5 ppb. It is interesting to note that the background reading of the sensor, the resistance at the zero time point, immediately increased by 20% as the film was placed into the exposure chamber, indicating a background level of nicotine before engaging the smoking apparatus. Prior to this experiment, the smoking chamber had been in constant use for 8 hours and deliberately not cleaned in the 2 hours prior to its application in the current experiment. The sensor was capable of measuring nicotine that was outgassing from the plastic chamber walls, an event labeled as "third hand smoke" when this event occurs in inhabited rooms and automobiles (Sleiman, et al. (2010) *PNAS* 107:6576-6581).

Figure 13:
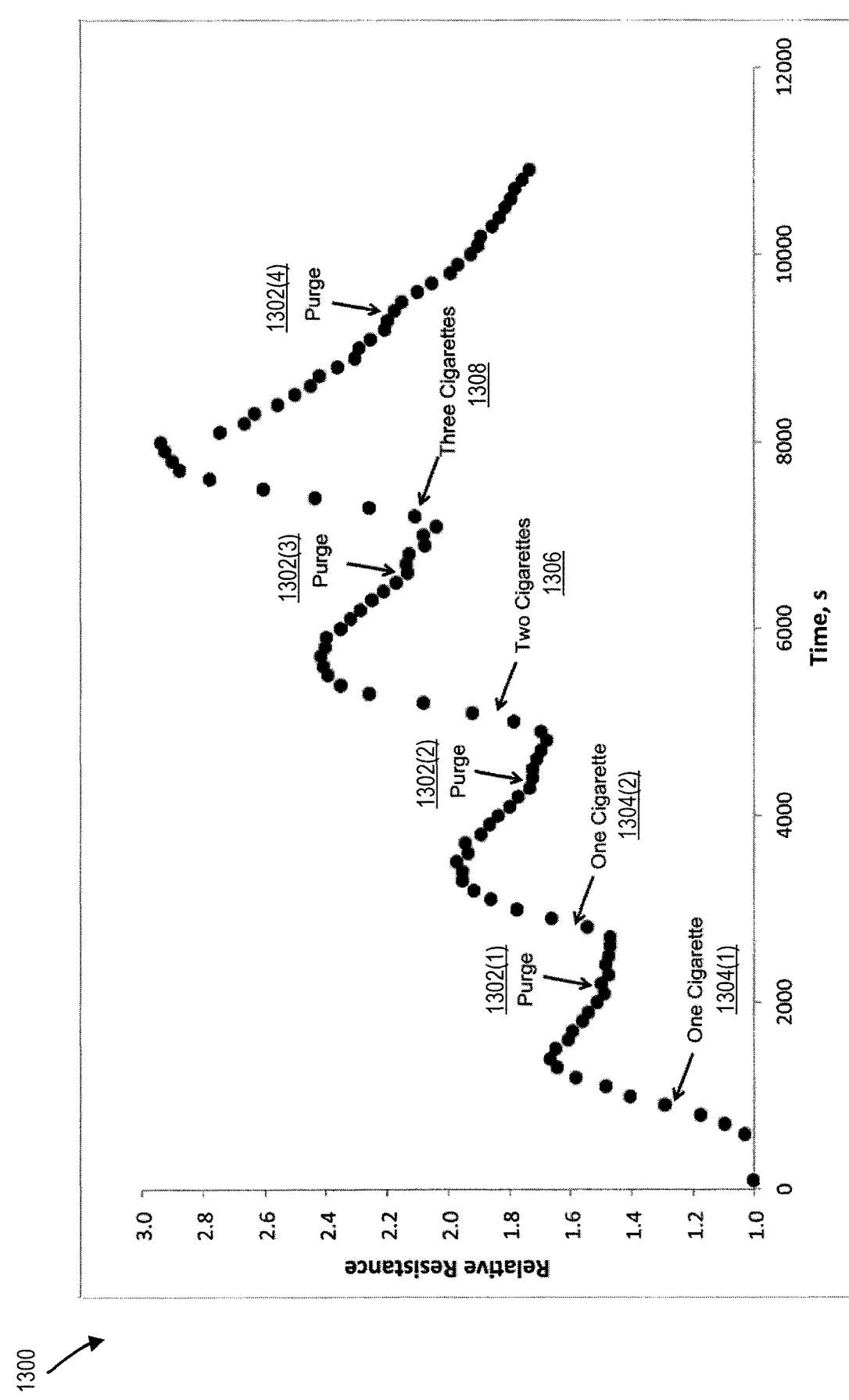
FIG. 13 shows the response of a nicotine sensing device, exemplary of the sensing device of FIG. 7, to a series of cigarette smoke exposures.

Plot 1300 of FIG. 13 demonstrates a set of sequential exposures in the Teague system, using varied number of simultaneously smoked cigarettes followed by a brief fresh air blowout (sections 1302(*i*)). Cigarettes were smoked over a period of eight minutes during which the sidestream smoke filled air from the smoking device was mixed with an equal volume of fresh air and fed into the exposure chamber. Following the extinguishing of the consumed cigarette, fresh air was blown into the exposure chamber for a period of six minutes. The decrease in resistance during the fresh-air phase shows that nicotine is desorbed from the sensor, restoring the resistance to a smaller value. The slopes of the rising signals are also related to the number of cigarettes simultaneously consumed. The system provides nominal dynamic concentrations of 0.75 ppb and 1.11 ppb of nicotine from sidestream smoke generated by two and three cigarettes, respectively. The initial slopes for the three different smoking levels were $9.62 \times 10^{-4} \Omega_{rel} s^{-1}$ (510 ppb), $1.63 \times 10^{-3} \Omega_{rel} s^{-1}$ (1030 ppb), and $1.72 \times 10^{-3} \Omega_{rel} s^{-1}$ (1,100 ppb), respectively, during consumption of one (sections 1304(*i*)), two (section 1306), and three cigarettes (section 1308). Note the agreement between the slopes in FIGS. 12 and 13 for a single cigarette and the measured increases in nicotine exposure for multiple cigarette exposure. Sensor fatigue caused by the insufficient 'off time' to remove nicotine from the sensor was observed for the final cycle shown in the figure. However, the final exposure cycle, with a longer smoke-free period, indicated that a return approximately to the original baseline was possible. Indeed, a resistance measurement made several hours after completing the experiments resulted in a value nearly equal to the initial resistance. It was noted that the first, single cigarette consumed increased the signal by ~60% and second, consecutive single cigarette furthered the increase by 32%. The next sample involved two cigarettes and resulted in a 40% signal increase with a final sample of three cigarettes and a 42% increase in resistance. The "blow out" phase returned the signal to approximately the resistance measured after the first experiment.

Figure 14:
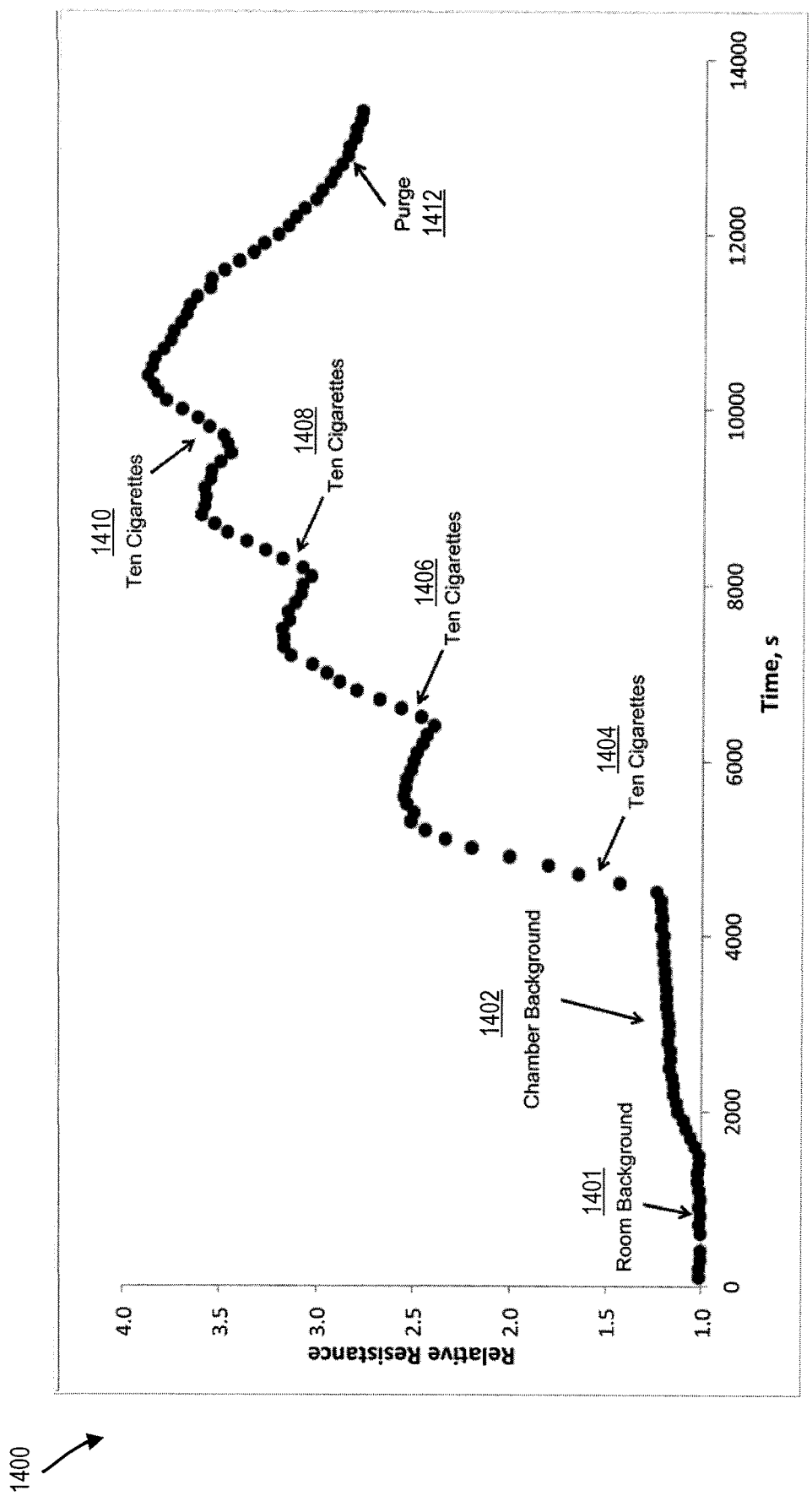
FIG. 14 shows the response of a nicotine sensing device, exemplary of the sensing device of FIG. 7, to a series of very strong cigarette smoke exposures.

Plot 1400, FIG. 14 contains the results from several successive runs in which 10 cigarettes (nominally providing 3.16 ppb of nicotine) were simultaneously smoked in order to test the response and recovery in a heavy smoking situation. The sensor background resistance was measured in ambient room air (section 1401) prior to insertion in the exposure chamber, providing a clear visualization of the ability to detect nicotine from the chamber walls (section 1402). The first 10-cigarette burn (section 1404) resulted in a steep increase with a slope of $1.91 \times 10^{-3} \Omega_{rel} s^{-1}$ (1,000 ppb), less than expected based on the previous figures but reflecting a saturation of easily reached binding sites near the surface of the sensor. After a six minutes delay (following cigarette extinguishment), a new burn was begun (section 1406), followed by two additional ten cigarette exposures sections 1408 and 1410). The absence of significant recovery time post-exposure decreased the increase in signal (although the third and fourth exposures provided similar increases) with measured changes in resistance of 110%, 25%, 15% and 9%. The fresh air purge at the end of the experiment did lower the signal substantially (section 1412). The intention of this particular experiment was to saturate the sensor, exposing it to levels of tobacco smoke that would unlikely be encountered if used as a personal sensing device (given air flow) or even if used as a room-level monitor, given the unlikelihood of such intense exposure within such a small space. The repeated 10-cigarette exposure within the 1 m3 volume of the smoking chamber would rival that of the smokiest bar with no ventilation at all. Most importantly, this particular study indicated that the film is sensitive to its environment, even if the ambient atmosphere has a relatively heavy concentration of smoking generated nicotine.

This analysis demonstrated that a chemiresistor based on a polyaniline film and interdigitated electrodes successfully monitors nicotine to provide a real time indication of exposure to second hand cigarette smoke. The polyaniline film was shown to be sensitive to the number of cigarettes consumed, demonstrated reasonable recovery between exposures and was functional in the presence of simulated heavy smoking. The detection of nicotine outgassing or "third hand smoke" was also demonstrated to be feasible using the polymer film assembly.

Example II

Molecularly Imprinted, Protonated, Conductive Polymer for Formaldehyde Detection Using phase inversion, formaldehyde cavities were created in a polyaniline (PANI)-Nylon 6 composite film. Films were produced by dissolving 0.2 g of PANI, 0.2 g of Nylon 6 and 20 μl of formaldehyde in formic acid. The formic acid dissolved the composite and formaldehyde to form a rigid polymer-formaldehyde network. After sufficient mixing, the imprinted polymer solution was uniformly spin-coated onto a glass substrate to form a thin film. After making the formaldehyde imprinted films, the formaldehyde molecules were extracted from the film aerially, leaving behind formaldehyde-specific receptor sites that were capable of molecular recognition and binding of formaldehyde molecules with remarkable specificity.

Infrared spectra analysis conclusively indicated that formaldehyde molecules bind to the PANI-Nylon 6 composite through strong hydrogen bonding due to the presence of an elongated carbonyl group at 1722 $cm^{-1}$. This peak was present in the imprinted polymer composite and noticeably absent in the control. This analysis indicated that PANI-Nylon 6 was successfully imprinted with formaldehyde. Moreover, the intensity of the peak indicated the efficacy of the imprinting process.

Changes in electrical resistance of imprinted polymer and control polymer following controlled exposure to formaldehyde vapor were determined using lithographically patterned interdigitated electrodes. The results of this analysis indicated that because the imprinted polymer had formaldehyde-specific cavities, it was able to selectively adsorb the formaldehyde molecules, which caused a dramatic increase in resistance of the film. In contrast, the control film with no cavities exhibited a relatively insignificant increase in electrical resistance in response to the formaldehyde vapor.

This demonstration proves use of the imprinted polymer for the sensing material in a sensing device for detecting airborne formaldehyde.

Composite Polymer with Protonated Conductive Component and Targeting Additive

Figure 15:
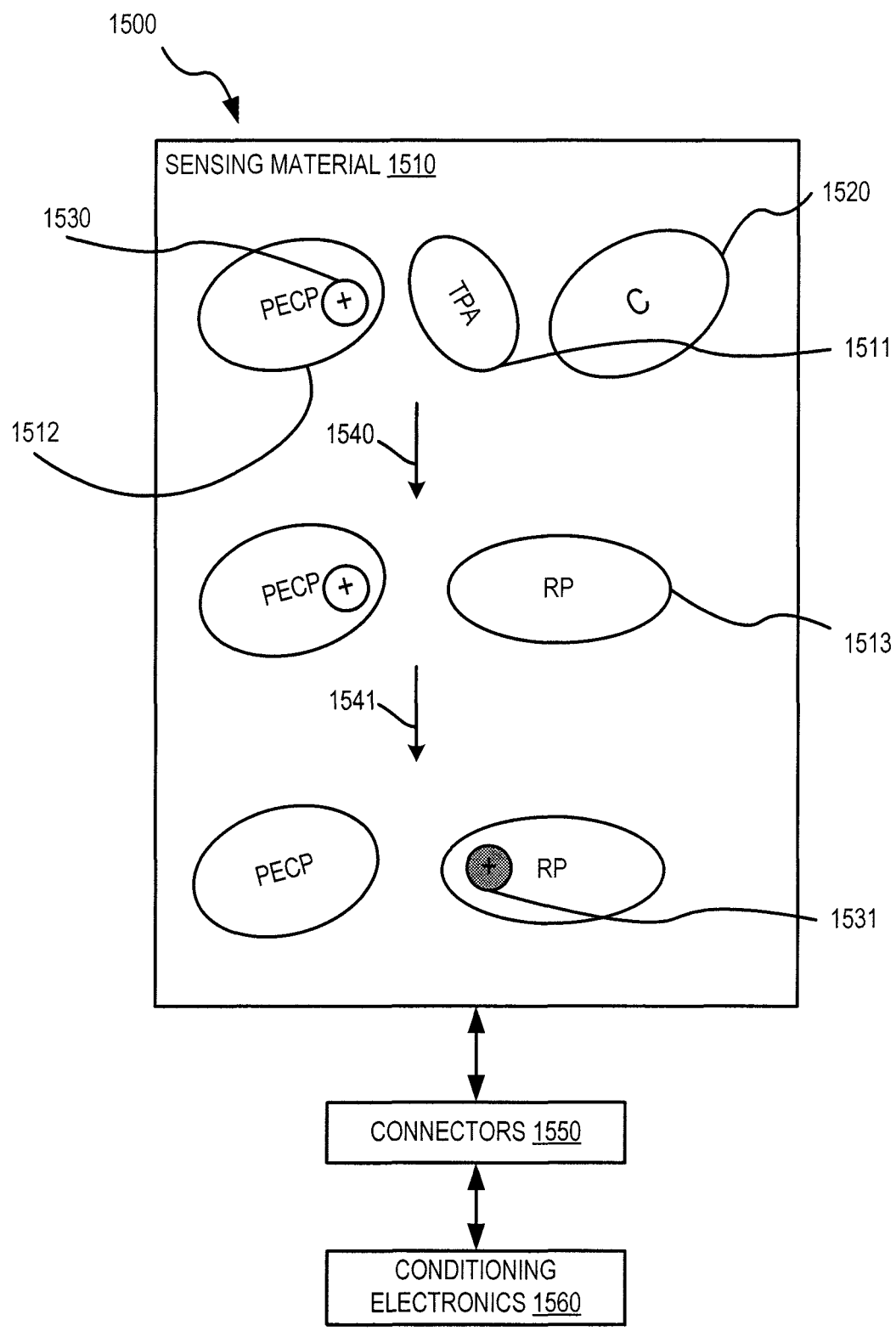
FIG. 15 illustrates an embodiment of a sensing device, based on a composite polymer, for detection of airborne contaminants.

FIG. 15 illustrates a sensing device 1500 having a sensing material 1510 (e.g., sensing material 611 of FIG. 6), which is a composite polymer including a targeting polymer additive (TPA) 1511 and a protonated, electrically conductive polymer (PECP) 1512. Targeting polymer additive 1511 has an affinity for reacting with an airborne contaminant 1520 (process indicated by arrow 1540), producing a reaction product (RP) 1513 capable of taking up a proton 1530 from protonated, electrically conductive polymer 1512 (process indicated by arrow 1541; proton lost to reaction product 1513 labeled 1531), thereby deprotonating sensing material 1510. Conditioning electronics 1560 (e.g., conditioning electronics 613 of FIG. 6) interrogates sensing material 1510 via connectors 1550 (e.g., connectors 612 of FIG. 6). The deprotonation of sensing material 1510, due to binding of airborne contaminant 1520 therewith, leads to a change in the electrical properties of sensing material 1510, which is measured by conditioning electronics 1560.

Example III

Formaldehyde Detection Using Composite Polymer with Targeting Component and Protonated, Conductive Component This example illustrates a specific embodiment of sensing device 1500 of FIG. 15, in which formaldehyde in the ambient air is detected in real time using a protonated, composite polymer film consisting of protonated PANi (e.g., protonated, electrically conductive polymer 1512 of FIG. 15) and PEI (e.g., targeting polymer additive 1511 or FIG. 15).

Materials and Methods.

Poly(aniline) was purchased from Polysciences, Inc. as the undoped, emeraldine base form with a molecular weight of 15,000 and a conductivity of $10^{-10}$ S/cm. Branched poly(ethyleneimine), PEI, with a molecular weight 70,000 was obtained from Alfa-Aesar as a 30% aqueous solution. Formic acid, >98%, was purchased from EMD Chemicals and used to dissolve the polymers prior to spin casting. Formaldehyde was purchased from Fisher Scientific as formalin solution (37% formaldehyde/10% methanol/53% water). All reagents were used as received without any further treatment.

The polymer films for detecting formaldehyde were spin-cast composites of PANi and PEI. PANi, which in its conductive form is insoluble. However, the emeraldine base may be dissolved in several solvents, including the formic acid used in this research; PEI is also soluble in formic acid. The formic acid solvent also acts as a primary dopant for PANi. Based on previous experiments, the spin casting solution was produced as a 5% by weight solution in each of the two polymers. PEI serves to create a more porous film as demonstrated in the characterization subsection. A number of functionalized PANi derivatives have been reported in the literature; however, an inexpensive sensing device for the target formaldehyde is desired, and the use of a specialized polymer would considerably raise costs. Hence, development was restricted to readily available materials.

The conductive sensors were constructed on oxidized silicon substrates with the PANi/PEI composite film as the active element above the electrode. Prime grade silicon wafers with a 5000 Å thermally deposited oxide layer were used for the substrate. The oxide layer ensures isolation of the interdigitated electrodes from the silicon surface. These films were patterned by photolithography and subsequently wet etched to produce the final electrodes with a total area of 376 mm2, following vapor deposition of 1000 Å of chromium and the 200 Å overlayer of nickel. Chromium is usually employed as the initial metal layer in order to improve adhesion of the actual conductive layer. The selection of nickel as the conductive layer was somewhat arbitrary; however, its conductivity is within a factor of three of that of gold and its use for the contact pads provided a soft, but rugged connection to the sensor mounting clips. Lift off was accomplished using acetone, with final rinses of water. The electrode was patterned into an interdigitated grid, as utilized in Example I above and illustrated in FIG. 8, with 40 µm fingers and 20 µm spacing. Next, the PANi/PEI polymer layer was spin-coated onto the electrode. An aliquot of 1 mL of solution was dropped onto the electrodes, and allowed to spread for 20 s. The spin-coater was then brought up to 1800 rpm for 30 s. This resulted in the deposition of films with a typical thickness of 300 nm. These conditions were chosen based on preliminary experiments. After this treatment, background resistance values are measured, and the sensor was ready for use in binding studies. Morphology of the thin films was investigated by scanning electron microscopy using a FEI Co. XL-30 ESEM-FEG field emission gun, environmental scanning electron microscope.

Two different laboratory test chambers were used in this study. The first, static chamber uses the vapor pressure of the analyte over the liquid as the source of the gaseous sample, while the second, vapor chamber relies on evaporation of the complete formalin sample in air after injection into the chamber far from the mounted film. The static sample system consists of a small nylon box, containing spring-mounted electrodes and an approximately 3 $cm^3$ well that is filled via a syringe through a septum. The sensor assembly was placed on the electrodes above the well and a nylon cover was secured using a torque wrench to ensure reproducible pressure of the sensor against the spring-mounted electrodes. Formalin (1 mL) at a known temperature was injected into the well and the response of the sensor was recorded. To follow the recovery of the sensor after exposure to formaldehyde, dry nitrogen was passed through the well to evaporate the sample. The change in the resistance of the sensor was measured using a multimeter connected to a laboratory computer.

The vapor chamber was based on a system reported by Zhang et al. (Zhang et al. (2011) *Sensor. Actuate. B Chem.* 152:316-323). An ~8 L cylindrical chamber was outfitted with a fan at the bottom and a cover that allows for a sensor holder so that the device is located approximately halfway along the 30 cm length. The cover also contains a port through which a microliter syringe may be inserted and a second port that allows mounting of a thermocouple; the reported temperatures are the chamber internal temperatures as measured by this thermocouple. Electrical contact was made between sample device and the holder, the fan was switched on and a small quantity of formalin (0.1-5 µL) was injected. Evaporation of the sample was very fast and the film detected the vapor nearly instantly. The chamber was not evacuated prior to use, so that the formaldehyde vapor was diluted with air at atmospheric pressure. The change in resistance was monitored using the same multimeter and computer as for the static chamber.

The physical property associated with presence of the target molecule in the film is the change in the resistance. Sensor functionality depends upon detecting differences in this property as a function of the adsorption of the target formaldehyde molecule onto the device. Numerous films/devices were tested using formalin both in the small static chamber and in the vapor chamber. The response of the sensing film to potentially interfering molecules was also examined. The resistance, R, of the polymer film was measured via a Keithley Model 2100 6½ Digit Multimeter. During the measurement, a constant current of 1 mA was applied and the voltage drop across the film was recorded, providing a resistance value via Ohm's law. Total dissipated power within the film was less than 500 mW. Four point measurements were found unnecessary and all of the reported data were obtained using two contacts, an inherently simpler measurement. Noise was not found to be an issue, therefore, the simpler DC measurement was employed over lower noise, but more complicated AC data acquisition. The signal to noise for the lowest volume of injected formalin was estimated from the results to be 6.3, including the effect of signal drift. While direct measurement was used in the data reported here, when the sensor is employed in a real application of a sensing device, a DC bridge is used to determine resistance, since a DC bridge is not significantly noisier than the AC type (Fluke Technical Note, AC versus DC: The Truth, 2012).

Data are taken at a rate of 1 Hz over a period of several minutes or more. The resistance increases by as much as 6 kΩ (a factor of 5) from its background value prior to exposure through to a plateau associated with the level of formaldehyde in the static sample chamber. Larger changes in R, greater than 10 kΩ, were observed in the vapor system over a 1-min sampling time. Data are reported as the change in resistance, referenced to the initial background value. The results demonstrate that the change in the resistance value, and the rate of change in the resistance (the slope), are proportional to the quantity and identity of the analyte adsorbed. Either of the quantities, AR or the slope, may be used to quantify the formaldehyde; the change in resistance for a fixed time is reported in the data presented here.

Results and Discussion.

The morphology of the film surface was investigated by scanning electron microscopy (SEM) of films produced on glass or oxidized silicon under the coating conditions described above. The pure PANi film is very smooth with no visible porosity, one expects that most adsorption activity would occur at the surface of the film. The composite film shows highly developed porosity, presumably templated by the presence of the PEI, which is known to produce fibrous material. Since the coating is now a composite, the extent of the PANi reporting polymer available for adsorption of the analyte is significantly increased and this material is predicted to offer an improved sensor basis. Experiments demonstrated that this prediction was valid and that the composite provided significantly greater responsivity to the target molecule. The porous composite film provides an ideal material for adsorption of the target formaldehyde molecule in the vapor phase.

The vapor phase chamber was used to obtain a calibration of the device with respect to the amount of formaldehyde present in air. Zhang et al. (Zhang et al. (2011) *Sensor. Actuate. B Chem.* 152:316-323) have shown that utilization of such a device, with complete vaporization of the injected sample, provides the necessary data. Zhang et al. have further provided a formal equation that is used here to relate the gas phase formaldehyde concentration in air, C, to the injected volume of liquid formaldehyde, V. With the present parameters, the gas phase formaldehyde concentration is given by C=37.7 V (µL).

Figure 16:
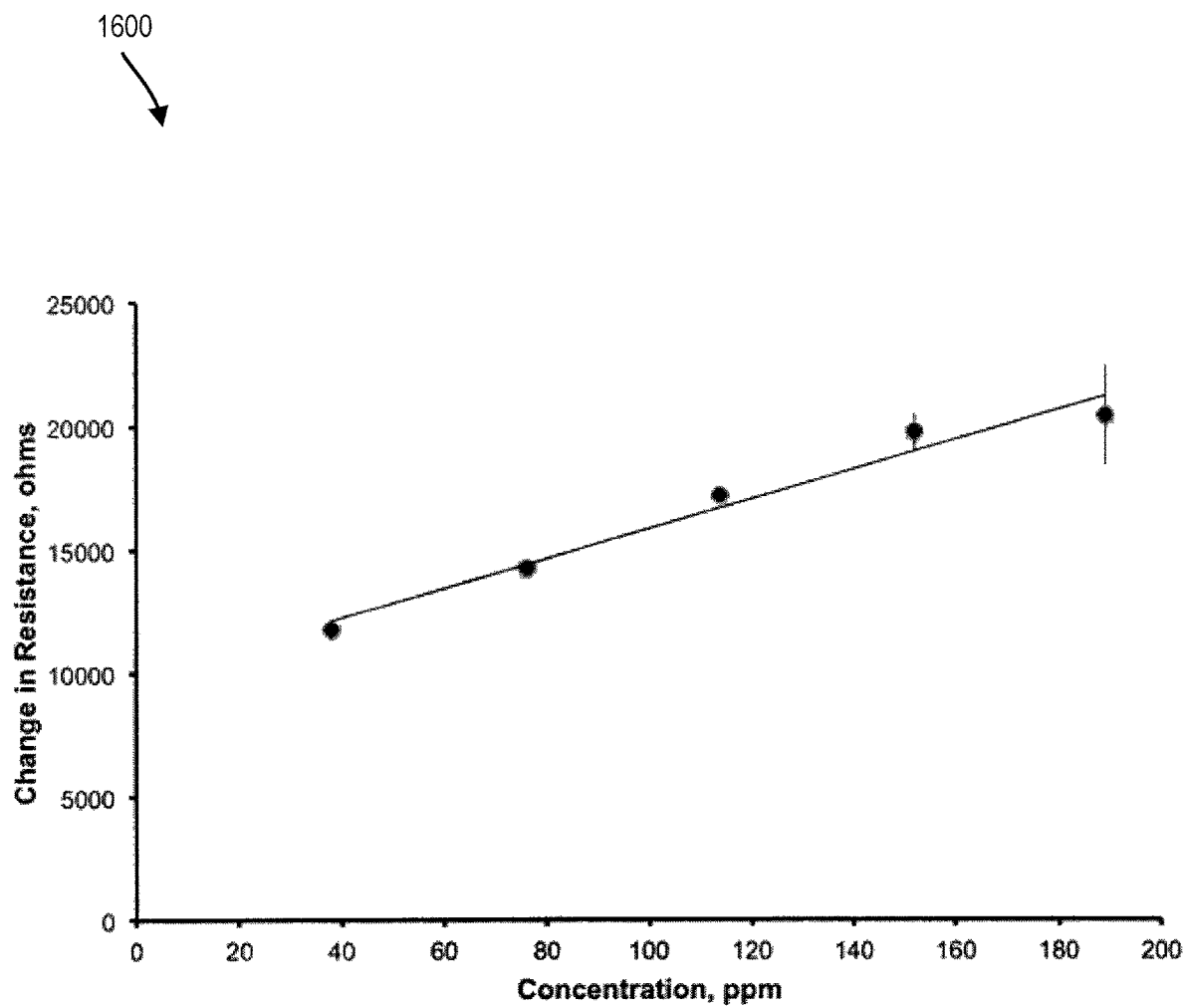
FIG. 16 shows a calibration curve for a formaldehyde sensing device exemplary of the sensing device of FIG. 15.
Figure 17:
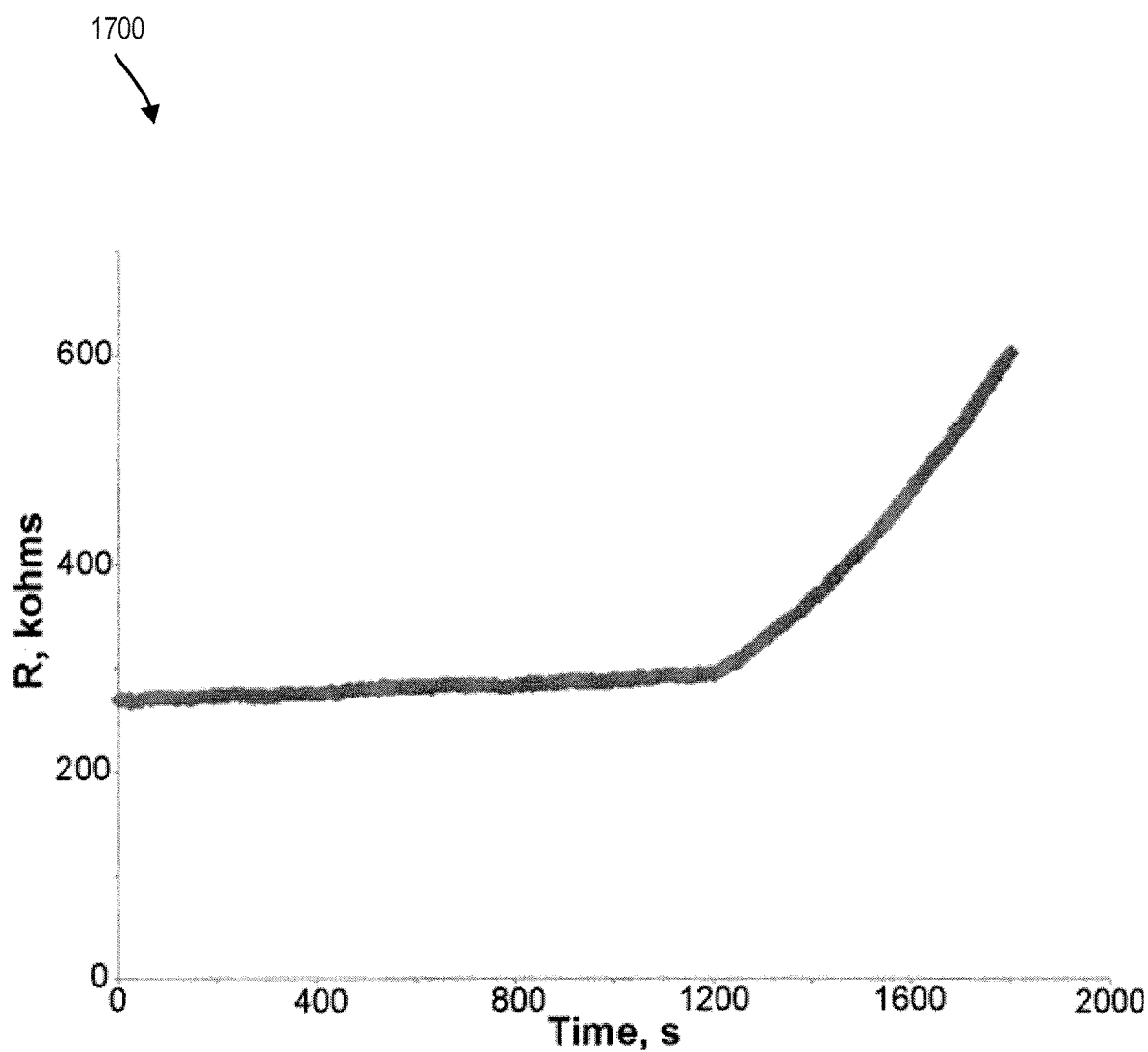
FIG. 17 shows the time evolution of the response of a formaldehyde sensing device, exemplary of the sensing device of FIG. 15.

Samples as small as 0.1 µL were injected, providing a minimum concentration of vapor phase formaldehyde of 4 ppm in air. This minimum sample size was not limited by the film response, but rather by the inability to reproducibly deliver smaller quantities to the chamber. The physical and chemical processes operating at the film surface and in the chemiresistor are complex, and thus a practical manner of calibration by recording the resistance after a 1 min post-injection delay was adopted. The resulting calibration curve is shown in FIG. 16. FIG. 17 shows a plot of the real time data for injection of a 5 µL sample of formalin at 22° C. As may be seen in the figure, the resistance continues to rise over the 10 min post-injection time frame provided in the figure. The film will continue to adsorb the target molecule as long sample remains in the nascent atmosphere and surface sites are available, making a choice of measurement time a necessity. A continuous signal rise over the course of at least 1 h was observed, at the range of concentrations used to generate data plots 1600 and 1700 of FIGS. 16 and 17. At least two measurements were made at each concentration point using a new sensor for each measurement and measurements were made with sensors from two different lithographic runs, each providing a curve such as that shown in FIG. 17. The signal at the 1-min mark was consistent across the different sensors measured within a range of 2-5% for the smallest volumes of sample, verifying the use of the 1-min sensing time. Larger repeatability errors are observed for larger volumes, reflecting the need for longer post injection, sample vaporization periods. Clearly, longer measurement times provide greater signal changes; practical use of the film necessitates making compromises in exposure time. For the target formaldehyde, a reversible reaction with a proton from PANi reduces the conductivity of the polymer and yields the detected signal as a change in R. While PEI is also protonated by the formic acid solvent in the preparation stage, PEI is not conductive and is present to provide the porosity of the film rather than a signal.

Due to the nature of the signal, an unconventional measure of responsivity was required, and thus the initial slope was employed as the indicator. This norm depends on the film characteristics and the parameters of the interdigitated electrode as well as the nascent concentration. At a concentration of 189 ppm at 25° C., the resistance increases at 278 $\Omega$/s over the minute of measurement. Recovery time is much faster with a typical return to baseline resistance in 20 s at this concentration after the 1 min exposure.

While both sensitivity and response are crucial components of any sensing element, the film to be employed in a practical device is to be specific or, at the least, more responsive to the desired target than any potential interfering molecule. Using the static chamber, the film was tested against six other molecules at 20° C. which resulted in resistance increases as resistance change per parts per million. The data presented for the test set indicates that formaldehyde is preferentially detected. The results are shown in Table 1. In testing, the most significant responses for potential interferents arose from ammonia, methanol and acetone, but with a response that is ~100 times less than that for formaldehyde.

The results presented in Table 1 provide evidence that the relative humidity is not a critical factor in the measurement of formaldehyde vapor concentration. If one uses Eq. (1) to calculate the total mass of formalin vaporized in the vapor chamber and the composition of the formalin solution to apportion the total mass to formaldehyde, water and methanol, one may compute a predicted signal based on the response provided in Table 1 for each component. Such a calculation indicates that, for example in the case of the 5 μL injection, 1% of the resistance change could be attributed to water from the formalin and 0.2% of the signal to methanol. While it is feasible to develop correction factors for humidity based on Table 1, the greatest possible interfering signal is still within the reported reproducibility shown in FIG. 16.

TABLE 1

| Test molecule | Resistance change in $\Omega$/ppm |
|---|---|
| Chloroform | $9.71 \times 10^{-4}$ |
| Acetone | $1.53 \times 10^{-3}$ |
| Dichloromethane | $1.60 \times 10^{-3}$ |
| Water | $2.12 \times 10^{-2}$ |
| Methanol | $3.26 \times 10^{-2}$ |
| Ammonia | $4.35 \times 10^{-2}$ |
| Formaldehyde | 3.95 |

Figure 18:
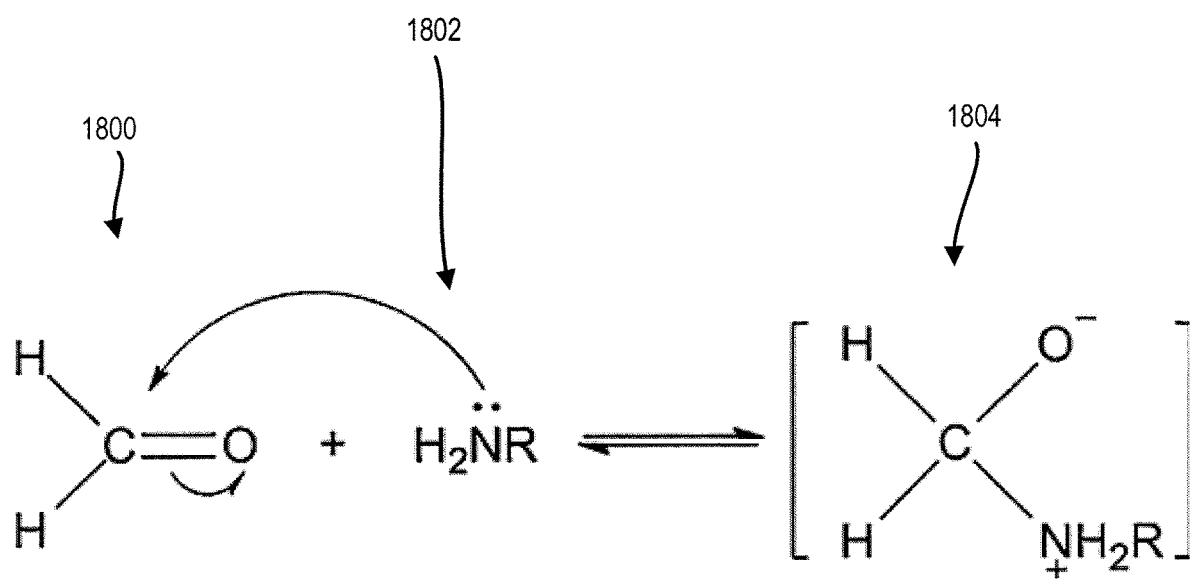
FIG. 18 shows a reaction occurring upon binding of formaldehyde to a sensing device exemplary of the sensing device of FIG. 15.

Following the adsorption of formaldehyde the following chemistry is believed to take place in the sensing film. Acid doping of PANi leads to the formation of nitrogen radical cation centers that provide p-type semiconduction and allow for its utility as a sensing platform. A nascent molecule exhibiting basicity as well as other molecules capable of extracting a proton from the doped polymer, such as formaldehyde, will decrease its conductivity. The inclusion of PEI as a component of the composite sensing film provides a chemical interaction or trapping site in addition to the increased porosity already noted herein. The formaldehyde carbon atom (e.g., formaldehyde 1800) is an electrophile that interacts with the nonbonding electrons on the primary amine functionalities of PEI (e.g., PEI portion 1802) to reversibly form a polymer bound adduct (e.g., adduct 1804) as shown in FIG. 18. Although rearrangement of this adduct to formation of an imine is theoretically possible, that reaction would be irreversible and the observation that formaldehyde readily desorbs from the film with a concurrent increase in film conductivity is an indication that the adduct does not further react to an imine. The PEI sequestration of the formaldehyde is followed by the abstraction of a proton from the doped PANi by the bound adduct and a concurrent increase in the resistance of the film. The intimate mixing of the PEI and PANi components in the composite film makes this reaction facile. To summarize, a chemical interaction with PEI traps formaldehyde in the film and allows for increased probability of a chemical interaction with the doped PANi. The PEI component, therefore, plays an active role in the selectivity and response of the sensor.

Dielectric Polymer

Figure 19:
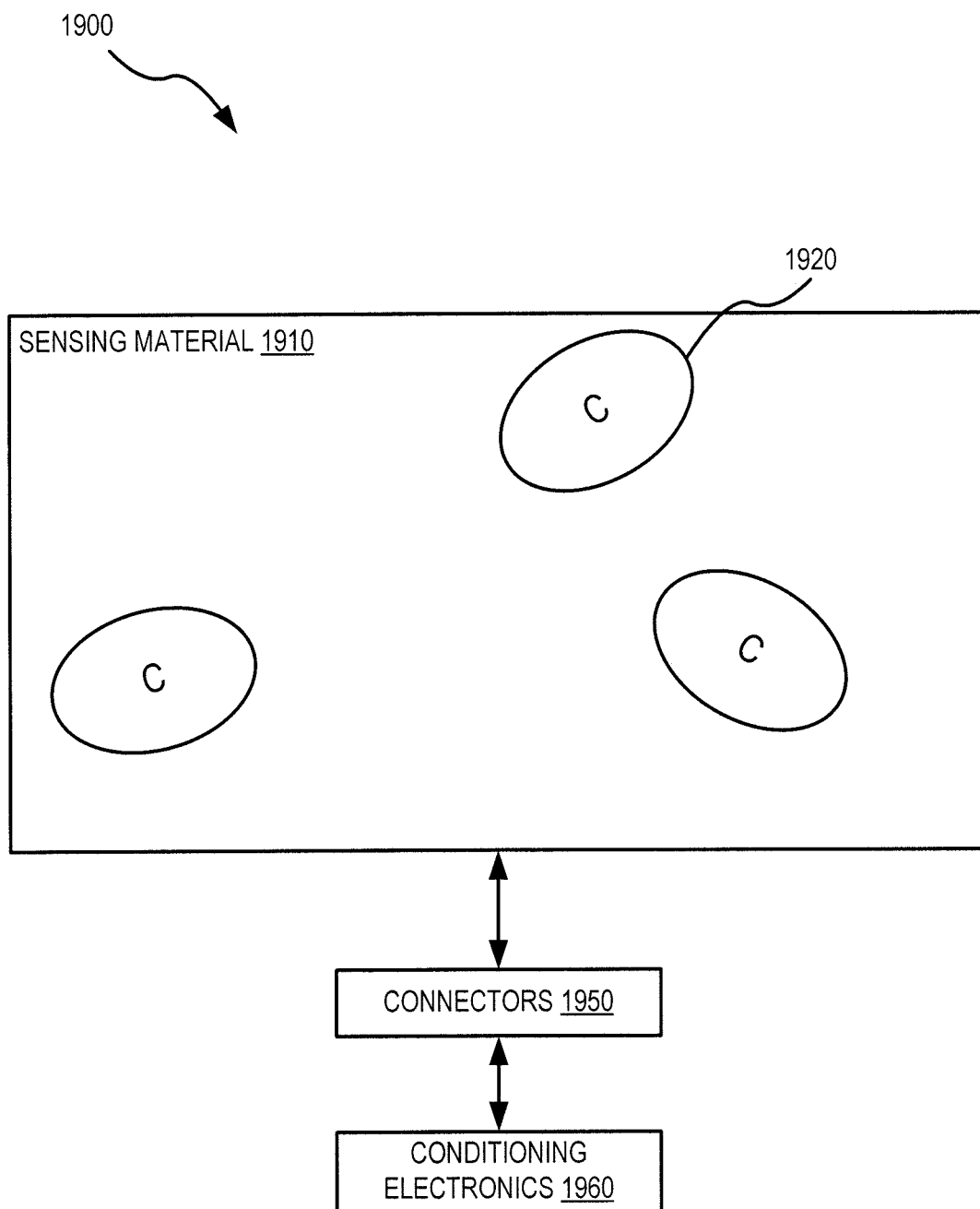
FIG. 19 illustrates an embodiment of a sensing device, based on a dielectric polymer, for detection of airborne contaminants.

In a sensing device 1900 illustrated in FIG. 19, a sensing material 1910 (e.g., sensing material 611 of FIG. 6) is a dielectric polymer with a binding affinity for an airborne contaminant of interest 1920. Upon binding of airborne contaminant 1920 to sensing material 1910, the properties of sensing material 1910 are modified. Sensing material 1910 is connected via connectors 1950 (e.g., connectors 612 of FIG. 6) to conditioning electronics 1960 (e.g., conditioning electronics 613 of FIG. 6), which may measure one or more of, for example, capacitance, dielectric dispersion, dielectric relaxation, dissipation factor, conductivity, dielectric constant, and resonance properties of sensing material 1910. The properties are for example measured as a function of a condition applied by conditioning electronics 1960.

A scan of the capacitance and/or dissipation factor as a function of the frequency of an AC electric field applied by conditioning electronics 1960 may change as a function of the amount of airborne contaminant 1920 adsorbed by sensing material 1910. Capacitive sensors known in the art and a suitable sensor configuration can be employed. In one example, the capacitive sensor is a sandwich-type electrode configuration, wherein sensing material 1910 is placed between two capacitor elements or electrodes. The electrode material may be chosen from any suitable conductor or semiconductor e.g., gold, platinum, silver, and the like. One or both of the capacitor elements may have features, e.g., slots, that allow for the airborne contaminant 1920 to come into contact with sensing material 1910. In an embodiment, a sandwich-type capacitive sensor is produced by depositing chromium on a glass, silicon or mica substrate by thermal evaporation. The chromium is patterned by photolithography and treated, subsequently, by wet etching. An insulating $SiO_2$ layer with a thickness between 40 nm and 200 nm is deposited onto the bottom electrode surface using an electron-gun thermal deposition technique. Subsequently, the sensing material is spin coated on the substrate surface. In the final step, a Cr film with a thickness of 70 nm is deposited on the molecular imprinted polymer film surface by thermal evaporation, followed with patterning by photolithography and wet etching.

Increased sensitivity and/or specificity of sensing device 1900 may be achieved by molecularly imprinting sensing material 1910 as illustrated in Example IV below.

Example IV

Production of Molecularly Imprinted Poly(4-Vinylphenol) Films for Detection of Nicotine or Cotinine The aromatic nature and hydrogen bonding potential make Poly(4-vinylphenol) (PVP) an ideal host matrix for molecularly imprinted polymers. The PVP films were produced by spin coating; a simple deposition technique that is sensitive to the composition and viscosity of the solution and the rotating speed of the plate (see, e.g., Bronside, et al. (1987) *J. Imaging Technol.* 13:122).

Solutions composed of 10 mL of methanol (Acros Organics; ACS Reagent Grade 99.8%) with 10 wt % of PVP powder obtained from Polysciences, Inc. (MW=22,000; $T_g$ 150° C.) and 5 wt % of nicotine or cotinine were nitrogen purged, covered, and stirred at room temperature for 24 hours. Control films were similarly produced, but without the nicotine or cotinine. Films were spin cast from these solutions onto 22 mm square glass microscope cover slips. Typically, the slides were prewashed with spectroscopic grade isopropanol and acetone prior to polymer deposition. The coating solution was dropped onto a stationary substrate and the spin coater was operated at 4000 rpm for 30 seconds with negligible ramp up time. The rotation spreads the solution evenly over the surface and also causes the solvent to evaporate leaving a thin film of material on the substrate. The concentration of PVP in the casting solution is the dominant variable for the film thickness, which increases rapidly with increasing concentration (solution viscosity). Cast films are quite stable and may be stored or used for an indefinite time.

The template molecule was removed from the film by immersion in deionized water for five hours. Nicotine (or cotinine) removal was confirmed by Fourier transform infrared spectroscopy (FTIR) measurements. Template reinsertion (or reinsertion of the complementary template molecule) was accomplished by immersion of the template extracted (or control) film in a 5 wt % solution of the molecule in deionized water for 2.5 hours. This reinsertion, as with the template removal procedure, is an equilibrium-controlled process and reinsertion occurs to approximately 50% of the initial concentration (via qualitative FTIR measurements). Additional immersion time was not found to increase the relative amount of template molecule reinserted into the film. FTIR spectra were recorded over a narrow region of interest, ~3400 cm for the OH stretch of PVP, which is missing when hydrogen bonded to nicotine or cotinine or ~1700 $cm^{-1}$ in the carbonyl region of cotinine, to confirm the interaction of the template with the polymer in the film. The surface topography of the films is characterized by average roughness measurements, $R_a$, using scanning force microscopy (SFM). It is defined as the average deviation of the profile from a mean line or the average distance from the profile to the mean line over the length of the assessment. The surface roughness, $R_a$, is given by the sum of the absolute values of all the areas above and below the mean line divided by the sampling length.

V. Combinations of Features

Features described above as well as those claimed below may be combined in various ways without departing from the scope hereof. For example, it will be appreciated that aspects of one sensing device/sensing material described herein may incorporate or swap features of another sensing device/material described herein. The following examples illustrate possible, non-limiting combinations of embodiments described above. It should be clear that many other changes and modifications may be made to the methods and apparatus herein without departing from the spirit and scope of this invention:

(A) A device for detecting airborne contaminants may include a protonated, electrically conductive sensing material with an affinity for binding with the airborne contaminant and electronics for measuring a property of the sensing material, where the property is sensitive to deprotonation.

(B) In the device denoted as (A), the sensing material may be capable of being deprotonated by the airborne contaminant.

(C) In the devices denoted as (A) and (B), the electronics may generate signals indicative of the airborne contaminant.

(D) In the devices denoted as (A) through (C), the airborne contaminant may deprotonate the sensing material by reacting directly with a protonated component thereof.

(E) In the devices denoted as (A) through (D), the sensing material may include a protonated, electrically conductive component and an additive with affinity for binding with the airborne contaminant.

(F) In the device denoted as (E), the airborne contaminant may deprotonate the sensing material by reacting with the additive to form a reaction product that deprotonates the sensing material.

(G) In the device denoted as (F), the reaction product may deprotonate the sensing material by reacting directly with the protonated, electrically conductive component.

(H) In the devices denoted as (A) through (G), the sensing material may include a thin film.

(I) In the devices denoted as (A) through (H), the sensing material may include a polymer film.

(J) In the devices denoted as (A) through (I), the sensing material may be molecularly imprinted.

(K) In the device denoted as (I), the polymer film may include a π electron-conjugated polymer.

(L) In the device denoted as (K), the polymer film may be molecularly imprinted.

(M) In the devices denoted as (A) through (L), the sensing material may include one or more of: polyalinine; polypyrrole; polythiophene; a derivative of polyalinine, polypyrrole, or polythiophene; and a copolymer of polyalinine, polypyrrole, polythiophene, or a derivative thereof.

(N) In the devices denoted (A) through (M), the property may be one or more of resistance, conductivity, capacitance, and a derivative thereof.

(O) The devices denoted as (A) through (N) may include an enclosure for protecting the device except for an opening exposing the sensing material to ambient air.

(P) The devices denoted as (A) through (O) may include a clock for time-stamping of the signals indicative of the airborne contaminant.

(Q) In the devices denoted as (A) through (P), the airborne contaminant may be a component of tobacco smoke.

(R) In the devices denoted as (A) through (Q), the airborne contaminant may be one or more of carbon monoxide, nicotine, 4-(methylnitrosamino)-1-(3-pyridyl)-1-butanone, acetaldehyde, and formaldehyde.

(S) In the devices denoted as (A) through (R), the electronics may include a processor for processing data of the property.

(T) In the devices denoted as (A) through (S), the electronics may include memory having data for correlating the property to a level of the airborne contaminant (U) In the devices denoted as (A) through (T), the electronics may include an interface for communicating visible, audible, and/or tactile information to a user.

(V) In the devices denoted as (S) through (U) the processor and memory may be integrated in a microprocessor.

(W) In the devices denoted as (U) and (V), the interface may communicate with the user through a remote computer.

(X) In the device denoted as (W), communicating with the user through a remote computer may include wireless communicating.

(Y) In the devices denoted as (U) through (X), the interface may generate an alert when the level of the airborne contaminant passes a threshold.

(Z) In the devices denoted (A) through (Y), the device may detect a plurality of airborne contaminants.

(AA) In the device denoted (Z), the sensing material may have multiple compositions each with affinity for binding with at least one of the plurality of airborne contaminants.

(AB) In the devices denoted (Z) and (AA), the electronics may measure properties sensitive to deprotonation of each of the multiple compositions.

(AC) A method for detecting at least one airborne contaminant may include determining a change in a property of a protonated, electrically conductive material exposed to ambient air with the airborne contaminant (AD) The method denoted as (AC) may further include determining the presence of the airborne contaminant based on the change.

(AE) The methods denoted as (AC) and (AD) may further include communicating with a computer remote from the material.

(AF) In the method denoted as (AE), determining may occur within the remote computer.

(AG) In the methods denoted as (AD) through (AF), determining may include determining an abnormal level of the airborne contaminant.

(AH) In the method denoted as (AG), determining an abnormal level may include detecting an abnormal electrical property.

(AI) The methods denoted as (AC) through (AH) may further include storing, in memory, data representative of a change of the property.

(AJ) The methods denoted as (AE) may further include downloading at least a portion of the data to a remote computer for determining, when the change exceeds a threshold.

(AK) In the methods denoted as (AD) through (AJ), determining presence may include determining a level of the airborne contaminant, and comparing the detected level to a predefined normal range.

(AL) The methods denoted as (AC) through (AK) may further include communicating to an end user if a change exceeds a threshold.

(AN) In the methods denoted as (AE) through (AM), communicating may include sending an alert.

(AO) In the method denoted as (AC), the material may define a plurality of compositions.

(AP) In the methods denoted as (AD) through (AN), the steps of determining may include determining change in a plurality of the compositions to detect presence of a plurality of airborne contaminants.

(AQ) In the methods denoted as (AC) through (AP), the property may be one or more of resistance, conductivity, and a derivative thereof.

(AR) In the methods denoted as (AC) through (AQ), the property may be sensitive to deprotonation of the material.

(AS) In the methods denoted as (AC) through (AR), the airborne contaminant may be a component of tobacco smoke.

(AT) In the methods denoted as (AC) through (AS), the airborne contaminant may be one or more of carbon monoxide, nicotine, 4-(methylnitrosamino)-1-(3-pyridyl)-1-butanone, acetaldehyde, and formaldehyde.

(AU) In the methods denoted as (AC) through (AT), the material may include a thin film.

(AV) In the methods denoted as (AC) through (AU), the material may include a polymer film.

(AQ) In the methods denoted as (AC) through (AV), the material may be molecularly imprinted.

(AR) A system for detecting airborne contaminants may include a data center and a plurality of sensing devices in remote communication with the data center.

(AS) In the system denoted as (AR), each of the sensing devices may have a protonated, electrically conductive sensing material with an affinity for binding with at least one of the airborne contaminants.

(AT) In the system denoted as (AS), each of the sensing devices may further be capable of being depronated by at least one of the airborne contaminants (AU) The systems denoted as (AR) through (AT) may further include electronics for relaying signals indicative of a sensing material deprotonation property to the data center.

(AV) In the systems denoted as (AR) through (AU), a user associated with any of the sensing devices may be notified of an abnormal level of at least one of the airborne contaminants.

(AW) In the systems denoted as (AR) through (AV), the data center may be configured to process data from the sensing devices to determine and report level of at least one of the airborne contaminants.

(AX) In the systems denoted as (AV) and (AW), the data center may notify by email or text message each user of abnormal levels, if any, occurring at the associated sensing device.

(AY) In the systems denoted as (AU) through (AX), the signals indicative of a sensing material deprotonation may be based on measurement of one or more of resistance, conductivity, and a derivative thereof.

(AZ) In the systems denoted as (AS) through (AY), the sensing material may be a thin film.

(BA) In the systems denoted as (AS) through (AY), the sensing material may be a polymer film.

(BB) In the system denoted as (BA), the polymer film may be molecularly imprinted.

(BC) The systems denoted as (AR) through (BB) may further include dielectric sensing devices.

(BD) In the system denoted as (BC), each of the dielectric sensing devices may have a dielectric sensing material with an affinity for binding with at least one of the airborne contaminants (BE) In the systems denoted as (BC) and (BD), each of the dielectric sensing devices may have a dielectric property sensitive to the binding of the at least one of the airborne contaminants therewith.

(BF) In the systems denoted as (BC) through (BE), each of dielectric sensing devices may further include electronics for relaying signals indicative of a dielectric property to the data center.

(BG) In the systems denoted as (BE) and (BF), the dielectric property may be one or more of capacitance and a derivative thereof.

(BH) In the systems denoted as (BD) through (BG), the dielectric sensing material may be a thin film.

(BI) In the systems denoted as (BD) through (BH), the dielectric sensing material may be a polymer film.

(BJ) In the system denoted as (BI), the polymer film may be molecularly imprinted.

(BK) In the systems denoted as (AR) through (BI), one or more of the sensing devices may be configured within a cell phone.

(BL) In the systems denoted as (AR) through (BK), the airborne contaminant may be a component of tobacco smoke.

(BM) In the systems denoted as (AR) through (BL), the airborne contaminant may be one or more of carbon monoxide, nicotine, 4-(methylnitrosamino)-1-(3-pyridyl)-1-butanone, acetaldehyde, and formaldehyde.

The changes described above, and others, may be made in the systems, devices and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. Device for detecting airborne formaldehyde, comprising:
    a bulk polymer film including (a) polyethylenimine having affinity for reacting with the airborne formaldehyde to form a first reaction product, and (b) a protonated, electrically conductive polymer having resistance sensitive to deprotonation from reaction with the first reaction product, the protonated, electrically conductive polymer including one or more of polyalinine, polypyrrole, polythiophene, a derivative of polyalinine, a derivative of polypyrrole, a derivative of polythiophene, a copolymer of polyalinine, a copolymer of polypyrrole, a copolymer of polythiophene;
    a pair of interdigitated electrodes on a surface of the bulk polymer film; and
    electronics for measuring the resistance of the bulk polymer film through measurement of direct-current resistance of the bulk polymer film between the pair of interdigitated electrodes.

2. Device of claim 1, the bulk polymer film being molecularly imprinted.

3. Device of claim 1, the protonated, electrically conductive polymer comprising polyalinine.

4. Device of claim 1, further comprising a clock for time-stamping measurement of the resistance of the bulk polymer film.

5. Device of claim 1, the electronics comprising:
    processor for processing measurements by the electronics of the resistance of the bulk polymer film,
    memory having data for correlating the measurements to a level of the airborne formaldehyde, and
    interface for communicating visible, audible, and/or tactile information to a user.

6. Device of claim 1, further comprising:
    a second bulk polymer film that is protonated and electrically conductive and has (a) affinity for binding with a second airborne contaminant different from the airborne formaldehyde, and (b) resistance sensitive to binding of the second airborne contaminant;
    a second pair of interdigitated electrodes on a surface of the second bulk polymer film; and
    second electronics for measuring the resistance of the second bulk polymer film through measurement of direct-current resistance of the second bulk polymer film between the second pair of interdigitated electrodes.

* * * * *